(12) United States Patent
Voorhees et al.

(10) Patent No.: US 12,005,001 B2
(45) Date of Patent: Jun. 11, 2024

(54) CORNEAL LENTICULAR INCISIONS WITH TRANSITION ZONES IN LASER-ASSISTED OPHTHALMIC PROCEDURES

(71) Applicant: AMO Development, LLC, Irvine, CA (US)

(72) Inventors: Andrew Voorhees, Sunnyvale, CA (US); Alireza Malek Tabrizi, Fremont, CA (US); Hong Fu, Pleasanton, CA (US); Cynthia Villanueva, San Jose, CA (US); Nima Khatibzadeh, Fremont, CA (US); Deepali Mehta-Hurt, Newark, CA (US); James Hill, Santa Ana, CA (US); Li Chen, Fremont, CA (US); Li Bing, Fremont, CA (US)

(73) Assignee: AMO Development, LLC, Irvine, CA (US)

( * ) Notice: Subject to any disclaimer, the term of this patent is extended or adjusted under 35 U.S.C. 154(b) by 266 days.

(21) Appl. No.: 17/445,308

(22) Filed: Aug. 17, 2021

(65) Prior Publication Data

US 2022/0054316 A1    Feb. 24, 2022

Related U.S. Application Data

(60) Provisional application No. 63/067,818, filed on Aug. 19, 2020.

(51) Int. Cl.
*A61F 9/008* (2006.01)

(52) U.S. Cl.
CPC .............. *A61F 9/00827* (2013.01); *A61F 2009/00872* (2013.01); *A61F 2009/00897* (2013.01)

(58) Field of Classification Search
CPC ........ A61F 9/00827; A61F 2009/00872; A61F 2009/00897; A61F 9/00829
See application file for complete search history.

(56) References Cited

U.S. PATENT DOCUMENTS

| | | |
|---|---|---|
| 7,131,968 B2 | 11/2006 | Bendett et al. |
| 10,369,052 B2 | 8/2019 | Fu |
| 10,779,988 B2 | 9/2020 | Fu et al. |

(Continued)

*Primary Examiner* — Joseph M Dietrich
*Assistant Examiner* — Ranjani Mari Sundaresan
(74) *Attorney, Agent, or Firm* — Johnson & Johnson Surgical Vision, Inc.

(57) ABSTRACT

In laser-assisted corneal lenticule extraction procedures, the lenticule incision profile includes anterior and posterior lenticule incisions, with one or more of the following features: plano transition zone outside the optical zone, to improve mating of anterior and posterior incision surfaces after lenticule extraction; shallow arcuate incisions above the anterior incision and near the lenticule edge, to improve surface mating; separate ring cut intersecting the anterior and posterior incisions in the transition zone, to reduce tissue bridges and minimize tear at the lenticule edges and facilitate easy lenticule extraction; larger posterior incision, which includes a pocket zone outside the lenticule edge, for better surface mating and bubble management during cutting; and a separate ring shaped pocket cut intersecting the pocket zone of the posterior incision, for bubble management. An entry cut can intersect either the pocket zone of the posterior incision or an entry extension zone of the anterior incision.

20 Claims, 11 Drawing Sheets

(56) References Cited

U.S. PATENT DOCUMENTS

| | | | |
|---|---|---|---|
| 2010/0130967 A1* | 5/2010 | Glasmacher | A61F 9/008 606/5 |
| 2012/0296321 A1 | 11/2012 | Frey et al. | |
| 2014/0081249 A1 | 3/2014 | Bischoff et al. | |
| 2015/0134316 A1* | 5/2015 | Dai | A61F 9/00804 703/11 |
| 2017/0172801 A1 | 6/2017 | Raksi | |
| 2017/0216091 A1 | 8/2017 | Bischoff et al. | |
| 2018/0000647 A1 | 1/2018 | Malek Tabrizi et al. | |
| 2018/0008461 A1* | 1/2018 | Fu | A61F 9/00829 |
| 2019/0015253 A1 | 1/2019 | Rathjen | |
| 2019/0060122 A1* | 2/2019 | Fu | A61F 9/00834 |

\* cited by examiner

CORNEAL LENTICULAR INCISIONS WITH TRANSITION ZONES IN LASER-ASSISTED OPHTHALMIC PROCEDURES

CROSS REFERENCE TO RELATED APPLICATIONS

This application claims the benefit under 35 U.S.C. § 119(e) of U.S. Provisional Patent Application No. 63/067,818, filed Aug. 19, 2020, which is incorporated herein by reference in its entirety.

BACKGROUND OF THE INVENTION

Field of the Invention

Embodiments of this invention relate generally to laser-assisted ophthalmic procedures, and more particularly, to systems and methods for forming corneal lenticular incisions with transition zone and other features.

Description of Related Art

Vision impairments such as myopia (near-sightedness), hyperopia and astigmatism can be corrected using eyeglasses or contact lenses. Alternatively, the cornea of the eye can be reshaped surgically to provide the needed optical correction. Eye surgery has become commonplace with some patients pursuing it as an elective procedure to avoid using contact lenses or glasses to correct refractive problems, and others pursuing it to correct adverse conditions such as cataracts. And, with recent developments in laser technology, laser surgery is becoming the technique of choice for ophthalmic procedures.

Different laser eye surgical systems use different types of laser beams for the various procedures and indications. These include, for instance, ultraviolet lasers, infrared lasers, and near-infrared, ultra-short pulsed lasers. Ultra-short pulsed lasers emit radiation with pulse durations as short as 10 femtoseconds and as long as 3 nanoseconds, and a wavelength between 300 nm and 3000 nm.

Prior surgical approaches for reshaping the cornea include laser assisted in situ keratomileusis (hereinafter "LASIK"), photorefractive keratectomy (hereinafter "PRK") and corneal lenticule extraction.

In the LASIK procedure, an ultra-short pulsed laser is used to cut a corneal flap to expose the corneal stroma for photoablation with ultraviolet beams from an excimer laser. Photoablation of the corneal stroma reshapes the cornea and corrects the refractive condition such as myopia, hyperopia, astigmatism, and the like. In a PRK procedure where no flap is created, the epithelium layer is first removed, and some stroma material is then removed by an excimer laser. The epithelium layer will grow back within a few days after the procedure.

In the corneal lenticule extraction procedure, instead of ablating corneal tissue with an excimer laser following the creation of a corneal flap, the technique involves tissue removal with two femtosecond laser incisions that intersect to create a lenticule for extraction. The extraction of the lenticule changes the shape of the cornea and its optical power to accomplish vision correction. Lenticular extractions can be performed either with or without the creation of a corneal flap. With the flapless procedure, a refractive lenticule is created in the intact portion of the anterior cornea and removed through a small incision.

SUMMARY

The present invention is directed to a method and related apparatus for corneal lenticule incisions that substantially obviates one or more of the problems due to limitations and disadvantages of the related art.

Additional features and advantages of the invention will be set forth in the descriptions that follow and in part will be apparent from the description, or may be learned by practice of the invention. The objectives and other advantages of the invention will be realized and attained by the structure particularly pointed out in the written description and claims thereof as well as the appended drawings.

To achieve the above objects, the present invention provides a method for forming a lenticule in a cornea of a patient's eye using an ophthalmic surgical laser system, comprising: operating the ophthalmic surgical laser system to generate a focused laser beam; and scanning the laser beam in the cornea to form an anterior lenticule incision and a posterior lenticule incision in the cornea, wherein the anterior lenticule incision includes a curved anterior optical zone, an anterior transition zone connected to and surrounding the anterior optical zone, and an anterior edge zone connected to and surrounding the anterior transition zone, wherein the posterior lenticule incision includes a curved posterior optical zone, a posterior transition zone connected to and surrounding the posterior optical zone, and a posterior edge zone connected to and surrounding the posterior transition zone, wherein the anterior optical zone and the posterior optical zone overlap each other in a top view along a direction parallel to an optical axis of the eye, the anterior transition zone and the posterior transition zone overlap each other in the top view, and the anterior edge zone and the posterior edge zone overlap each other in the top view, wherein the anterior and posterior lenticule incisions form the lenticule of corneal tissue between them, wherein the anterior edge zone and the posterior edge zone intersect each other to form an outer edge of the lenticule, and wherein the anterior transition zone and the posterior transition zone are parallel to each other and form a plano transition zone of the lenticule between them.

In some embodiments, the anterior and posterior transition zones are both parallel to an anterior surface of the cornea. In other embodiments, the anterior and posterior transition zones are both angled toward an anterior surface of the cornea as they extend radially outwards.

In some embodiments, the method further includes scanning the laser beam in the cornea to form a plurality of arcuate incisions in the cornea from an anterior surface of the cornea, wherein the arcuate incisions have arcuate shapes and are located inside of the outer edge of the lenticule in the top view, and wherein the arcuate incisions are substantially perpendicular to the anterior surface of the cornea and extend toward the anterior lenticule incision without intersecting the anterior lenticule incision.

In another aspect, the present invention provides a method for forming a lenticule in a cornea of a patient's eye using an ophthalmic surgical laser system, which includes: operating the ophthalmic surgical laser system to generate a focused laser beam; and scanning the laser beam in the cornea to form an anterior lenticule incision and a posterior lenticule incision in the cornea, wherein the anterior and the posterior lenticule incisions overlap each other in a top view along a direction parallel to an optical axis of the eye, wherein the anterior and posterior lenticule incisions form the lenticule of corneal tissue between them, and wherein the anterior and posterior lenticule incisions intersect each other to form an outer edge of the lenticule; and scanning the laser beam in the cornea to form a plurality of arcuate incisions in the cornea from an anterior surface of the cornea, wherein the arcuate incisions have arcuate shapes and are located inside of the outer edge of the lenticule in the top view, and wherein the arcuate incisions are substantially perpendicular to the anterior surface of the cornea and extend toward the anterior lenticule incision without intersecting the anterior lenticule incision.

In another aspect, the present invention provides a method for forming a lenticule in a cornea of a patient's eye using an ophthalmic surgical laser system, which includes: operating the ophthalmic surgical laser system to generate a focused laser beam; and scanning the laser beam in the cornea to form an anterior lenticule incision and a posterior lenticule incision in the cornea, wherein the anterior lenticule incision includes a curved anterior optical zone and an anterior transition zone connected to and surrounding the anterior optical zone, wherein the posterior lenticule incision includes a curved posterior optical zone, a posterior transition zone connected to and surrounding the posterior optical zone, and a posterior pocket zone connected to and surrounding the posterior transition zone, wherein the anterior optical zone and the posterior optical zone overlap each other in a top view along a direction parallel to an optical axis of the eye, and the anterior transition zone and the posterior transition zone overlap each other in the top view without intersection each other, and wherein the posterior lenticule incision is larger than the anterior lenticule incision in the top view; scanning the laser beam in the cornea to form a ring cut, wherein the ring cut extends along an entire circumference of the lenticule and intersects both the anterior transition zone and the posterior transition zone to form the lenticule of corneal tissue bound by the anterior and posterior lenticule incisions and the ring cut; and scanning the laser beam in the cornea to form an entry cut, wherein the entry cut extends in an angled direction with respect to the optical axis and extends from an anterior corneal surface to intersect either the posterior lenticule incision, or the anterior lenticule incision, or both the posterior lenticule incision and the anterior lenticule incision, and wherein the entry cut extends a predefined angular range in the top view.

In some embodiments, the posterior lenticule incision including the posterior optical zone, the posterior transition zone and posterior pocket zone is a spherical surface, a ring shaped portion of the anterior transition zone and a corresponding ring shaped portion of the posterior transition zone have matching curvatures and are separated from each other by a predefined distance.

In some embodiments, the ring cut is perpendicular to both the anterior transition zone and the posterior transition zone at respective intersection locations.

In some embodiments, the anterior transition zone and the posterior transition zone are non-parallel to each other, wherein a distance between the anterior transition zone and the posterior transition zone increases as the anterior and the posterior transition zones extend respectively away from the anterior and posterior optical zones.

In some embodiments, the entry cut intersects only the posterior lenticule incision in the posterior pocket zone.

In some embodiments, the anterior lenticule incision further includes an entry extension zone which extends outwardly from the anterior transition zone, wherein the entry extension zone extends a predefined angular range in the top view, wherein the entry cut intersects only intersects the anterior lenticule incision in the anterior entry extension zone, and wherein the predefined angular range of the entry cut is smaller than and located with the angular range of the entry extension zone.

In some embodiments, the method further includes: scanning the laser beam in the cornea to form a pocket cut, wherein the pocket cut extends along an entire circumference of the posterior lenticule incision and intersects only the posterior lenticule incision in the posterior pocket zone. The pocket cut is formed first, followed by the posterior lenticule incision, then the ring cut, then the anterior lenticule incision, and then the entry cut; or the posterior lenticule incision is formed first, followed by the pocket cut, then the ring cut, then the anterior lenticule incision, and then the entry cut.

In another aspect, the present invention provides an ophthalmic surgical laser system, which includes: a laser system configured to generate a pulsed laser beam; an optical delivery system configured to deliver the published laser beam to a cornea of a patient's eye, including a scanner system configured to scan a focus spot location of the pulsed laser beam within the cornea; and a controller configured to control the laser system and the scanner system to perform the above-described methods.

It is to be understood that both the foregoing general description and the following detailed description are exemplary and explanatory and are intended to provide further explanation of the invention as claimed.

BRIEF DESCRIPTION OF THE DRAWINGS

FIGS. 4A-4C illustrate corneal lenticule incisions with additional shallow arcuate incisions near the edges of the lenticule according to another embodiment of the present invention.

DETAILED DESCRIPTION OF PREFERRED EMBODIMENTS

Ophthalmic Surgical Laser System Configuration

Figure 16A:
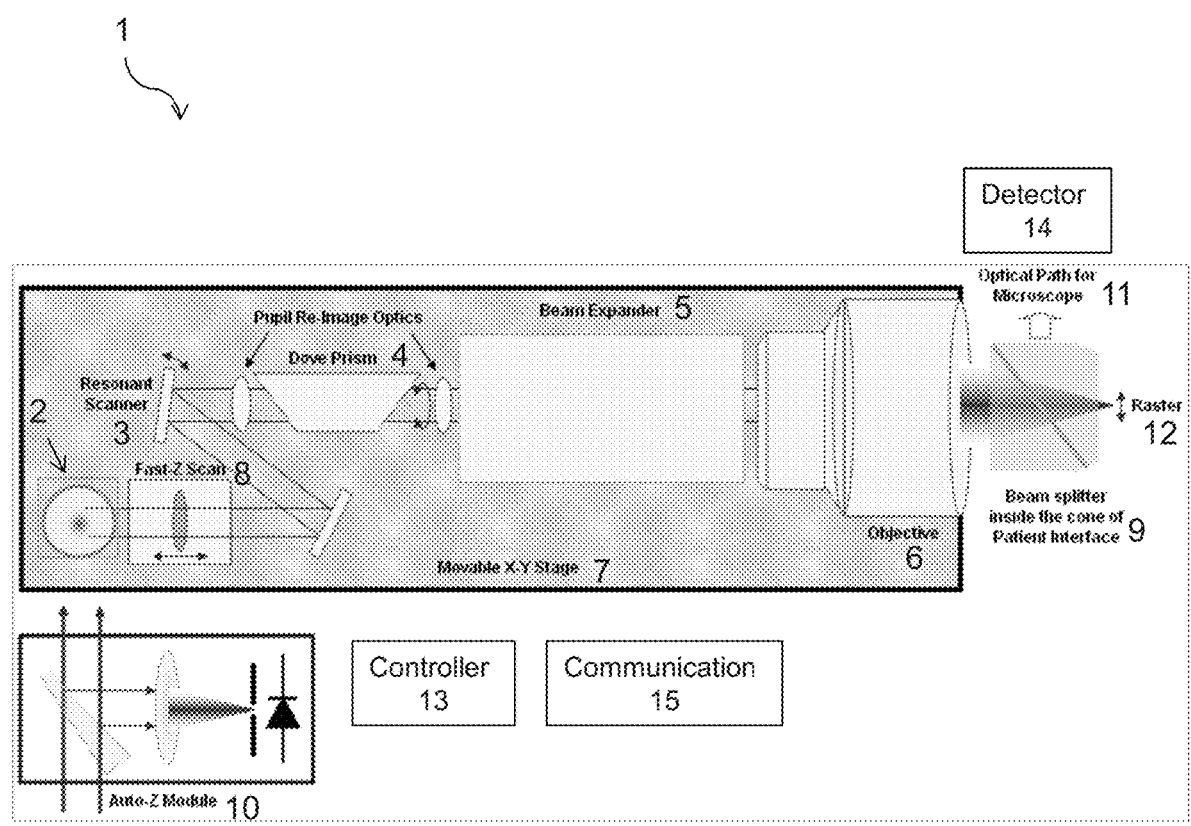
FIGS. 16A and 16B schematically illustrate two exemplary ophthalmic surgical laser systems in which embodiments of the present invention may be implemented.

Referring to the drawings, FIG. 16A shows an ophthalmic surgical laser system 1 suitable for making an incision in a target material such as a cornea of an eye. A laser source 2, such as a femtosecond laser, provides a pulsed laser beam 2A which may be used in optical procedures to treat the eye.

The system 1 further includes, but is not limited to, a high frequency scanner (such as a resonant scanner) 3 for scanning the pulsed laser beam to produce a scan line 12 of the pulsed laser beam, a scan line rotator 4 for rotating the scan line 12, a beam expander 5, an objective 6 for focusing the laser beam, an XY scan device 7 for deflecting or directing the laser beam on or within the target, a fast-Z scan device 8, a patient interface 9, an auto-Z device 10, a controller 13, and a communication module 15.

The resonant scanner 3 scans the pulsed laser beam at a high resonant frequency (e.g., thousands of Hz) to produces the scan line that extends in a lateral orientation (i.e. a direction perpendicular to the laser beam propagation direction Z) and having a desired length, for example, between 1 mm and 2 mm. The length of the scan line may be adjustable. The scan line rotator 4 may be implemented by a Dove prism, a Pechan prism, a set of mirrors, or the like, mounted on a rotating stage. By rotating the scan line rotator 4 around the Z axis, the lateral orientation of the scan line 12 is rotated, so that the scan line may be placed at any desired orientation in the XY plane (i.e., the lateral plane perpendicular to the laser beam propagation direction Z). The XY scan device 7 may be a movable XY scanning stage having the focusing objective 6 mounted thereon; the XY scan device 7 carries the objective 6 and moves it relative to the patient interface device 9, so as to move the center of the scan line 12 relative to the patient's eye in the XY directions. The fast-Z scan device 8 changes the depth (i.e. along the Z direction) of the laser focal spot location in the eye. Thus, the scan line rotator 4 modifies the lateral orientation of the scan line 12 while the moveable XY scanning stage 7 and the fast-Z scan device 8 move the center of the scan line in X, Y and Z directions. Because the scanning speed of the resonant scanner is typically much faster than the speed of the XY scanning stage and the fast-Z scan device, the scan line 12 may be referred to as a fast scan line, and the movement of the fast scan line in X, Y and Z directions may be referred to as a slow sweep.

The XY scanning stage 7 may be a motorized stage with two motors that drive its movements in the X and Y directions. Preferably, the XY scanning stage is a recoilless stage configured to reduce or eliminate mechanical vibration. The fast-Z scan device 8 may include a voice coil actuator that drives a lens in the Z direction. Movements of the lens lead to a focus depth change. The z-scan frequency may be between 50 Hz and 15,000 Hz.

The patient interface device 9 couples the patient's eye to the ophthalmic surgical laser system 1. The patient interface 9 may include a visualization beam splitter to reflect the light from the eye along an optical path 11 toward a video microscope or ocular microscope 14, to allow the eye to be imaged by an image detector of the microscope.

The auto Z module 10 measures a distal end surface of a lens of the patient interface coupled to the patient's eye and provides a depth reference for the fast-Z scan device 8 of the ophthalmic laser system. The auto Z module 10 may include, for example, a confocal detector.

The controller 13, which may be implemented by a processor executing suitable machine-readable program code and data stored in a non-volatile memory, is operably coupled to the various components of the system 1 including the laser 2, the fast-Z scan device 8, the resonant scanner 3, the scan line rotator 4, the XY scanning stage 7, the detector 14, and the communication module 15. The controller 13 is configured to direct these components of the system to output the focal spot of the pulsed laser beam in a desired pattern in the eye so as to modify the eye. The communication module 15 provides information to the operator of the laser system 1 at the system and/or remotely via wired or wireless data connection, and may include displays, user input devices such as keyboard, mouse, joystick, etc. The ophthalmic surgical laser system may additionally include an OCT (optical coherence tomography) device (not shown in FIG. 16A) which may be used to measure structures of the target (e.g. eye tissues).

Figure 16B:
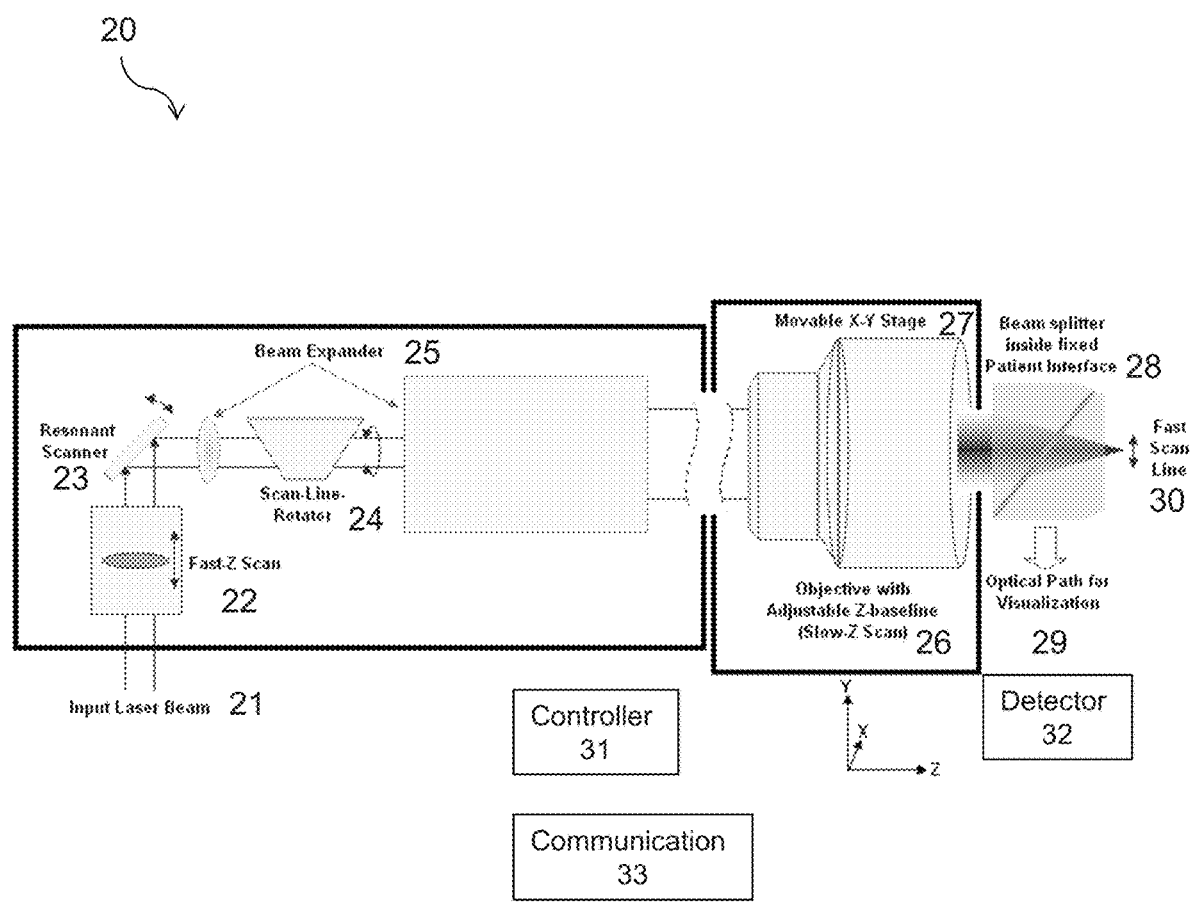

FIG. 16B shows an ophthalmic surgical laser system 20 suitable for making an incision in a target material such as a cornea of an eye. The system 20 includes, but is not limited to, a laser source (not shown) that generates an input pulsed laser beam 21, a fast-Z scan device 22, a resonant scanner 23 for producing a scan line 30 of the pulsed laser beam 21, a scan line rotator 24 for rotating the lateral orientation of the scan line 30, a beam expander 25, an objective with an adjustable focusing mechanism (slow-Z scanner) 26, a XY scanning stage 27 for deflecting or directing the pulsed laser beam 21 on or within the target, a patient interface 28 that may include a beam splitter, a controller 31, an image detector 32 disposed on an optical path 29 defined by the beam splitter of the patient interface, and a communication module 33. The slow-Z scanner 26 may be used to set the laser focal spot at a desired focal depth which may set the Z-baseline of the scan pattern.

One difference between the embodiment of FIG. 16B and that of FIG. 16A is that the XY scanning stage 7 in FIG. 16A carries both the objective 6 and other components including the fast-Z scan device 8, resonant scanner 3, scan line rotator 4, and beam expander 5, while the XY scanning stage 27 in FIG. 16B carries the objective 26 but not the other components mentioned above. Note that the in the system of FIG. 16A, the objective 6 may also be equipped with a slow-Z scanner (also represented by reference symbol 6).

Further details of ophthalmic surgical laser systems having the configurations shown in FIGS. 16A and 16B are described in commonly owned U.S. patent application Ser. No. 14/970,898, filed Dec. 16, 2015, entitled "Compact Ultra-Short Pulsed Laser Eye Surgery Workstation," and Ser. No. 14/865,396, filed Sep. 25, 2015, entitled "Systems and Methods for Lenticular Laser Incision," which are incorporated herein by reference in their entireties.

In other embodiments, an ophthalmic surgical laser system may employ other types of scanners, such as two orthogonal scanning mirrors, for scanning the laser beam in the transverse (XY) directions. Many such systems are known and their details are not described here.

Conventional Corneal Lenticule Extraction Methods

Figure 1A:
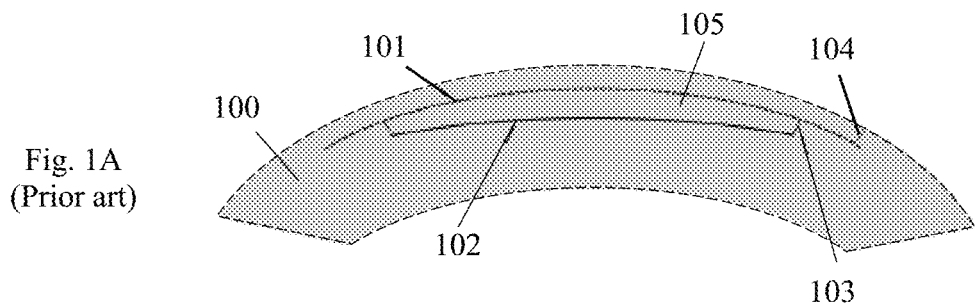
FIGS. 1A and 1B schematically illustrate the incisions formed in a conventional corneal lenticule extraction procedure.
Figure 1B:
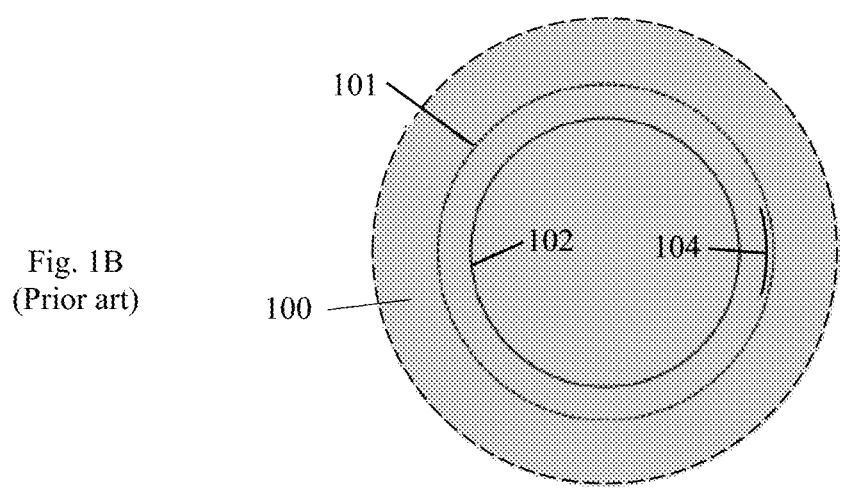

Corneal lenticule extraction is a known procedure for treating refractive errors. FIGS. 1A (side cross-sectional view) and 1B (top plan view) schematically the incisions formed in a conventional corneal lenticule extraction procedure for correcting myopia. As shown in FIGS. 1A and 1B, the lenticule incisions in cornea 100 include a spherical or toric cap cut (anterior lenticule incision) 101, a spherical or toric bed cut (posterior lenticule incision) 102, and a ring shaped side cut 103. The cap cut 101 is wider than the bed cut 102. The side cut 103, which is straight in the side view, connects the bed and cap cuts to isolate a lenticular volume 105 that can be extracted. An arcuate shaped entry cut 104 is made on one side to allow for extraction of the lenticule. As shown in the top view (FIG. 1B), the entry cut 104 is an arcuate shape that spans a predefined angular range.

Figure 1C:
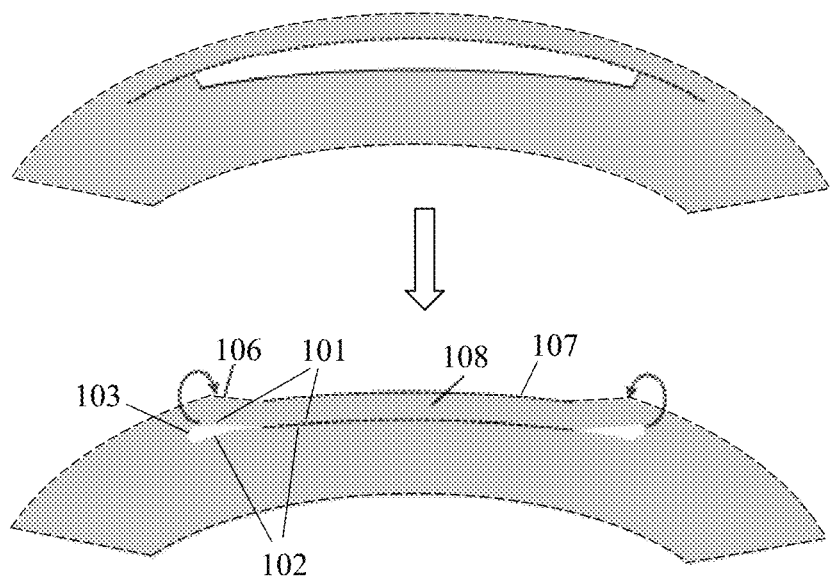
FIG. 1C schematic illustrates the expected draping of the cap over the bed after lenticule extraction using the conventional corneal lenticule extraction procedure shown in FIGS. 1A and 1B.

In corneal lenticule extraction surgeries, it is important that the anterior surface (cap) and the posterior surface (bed) in the remaining cornea mate perfectly following lenticule extraction. Proper draping of the cap over the bed is important to reduce light scattering and reduce the wound healing response following surgery. However, due to differences in the surface area of the cap and bed surfaces and changes in tissue tension due to the incisions, proper mating, or draping of the cap over the bed can be difficult to achieve, and fourth order spherical aberration often occurs as a result. As shown in FIG. 1C, after removal of the lenticule volume 105, the cap surface 101 bends around the side cut (as indicated by the arrows) to mate with the bed surface 102. This leads to a bulging 106 of the anterior corneal surface 107 near the border zone and the creation of a saddle shape, or fourth order spherical aberration. In such situations, appropriate mating of the bed and cap surfaces may only be achieved in the center area of the intended optical zone 108.

The first and second groups of embodiments of the present invention provide a lenticule cutting profile that can reduce these problems.

Corneal Lenticule Profile with Plano Transition Zone

To address the problem of improper surface mating and higher order spherical aberration, a first group of embodiments of the present invention provide corneal lenticule incision profiles that include a plano transition zone outside of the optical zone. The optical zone of the lenticule is the center portion of the lenticule that has a shape that imparts the desired optical power for refractive power correction. The surrounding plano transition zone has a uniform thickness, and may be either parallel to the anterior corneal surface or angled towards the anterior corneal surface, to further promote the mating of the bed and cap surfaces in the optical zone. The angling of the plano transition zone towards the anterior corneal surface also allows for the area of the posterior lenticule surface to be increased relative to the anterior lenticule surface, making the area of each cut more equal in the non-applanated configuration. The creation of the plano transition zone in the lenticule reduces the bulging of the anterior corneal surface near the edge of the lenticule after extraction, therefore reducing the fourth order spherical aberration.

Figure 2A:
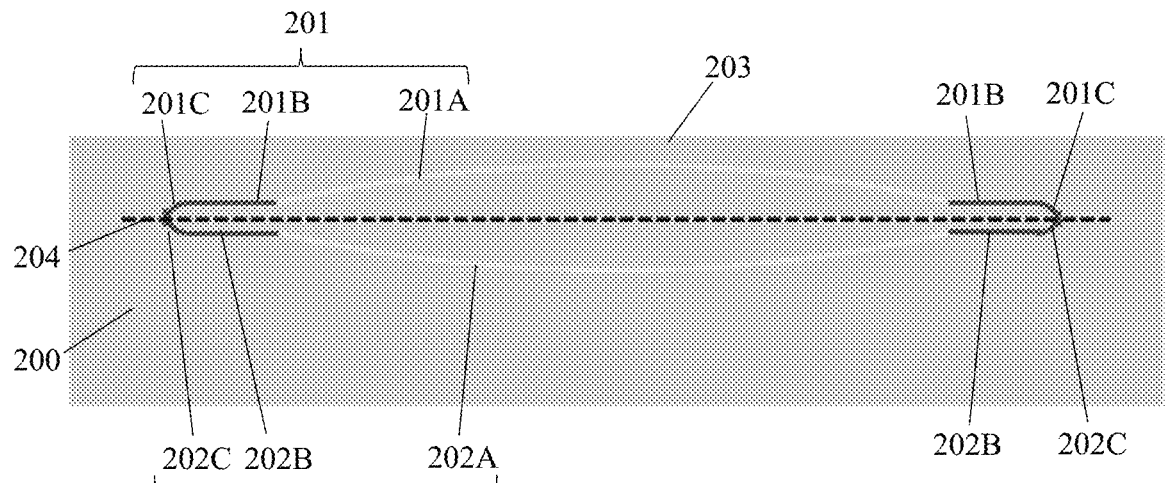
FIGS. 2A-2C illustrate corneal lenticule incisions with a plano transition zone in a lenticule extraction procedure according to an embodiment of the present invention.

FIG. 2A (a side cross-sectional view in a plane passing through the optical axis of the cornea) shows the incisions formed in a corneal lenticule extraction procedure for correcting myopia according to an embodiment of the present invention. In this embodiment, when performing the incisions, the cornea 200 is applanated by a patient interface device (not shown) that has a flat contact lens surface pressed against the anterior corneal surface 203 during the procedure. As shown in FIG. 2A, the incisions in cornea 200 include an anterior lenticule incision 201 and a posterior lenticule incision 202. The anterior lenticule incision 201 has a curved optical zone 201A (anterior optical zone) in the center, a transition zone 201B smoothly connected to and surrounding the anterior optical zone, and an edge zone 201C smoothly connected to and surrounding the transition zone. Similarly, the posterior lenticule incision 202 has a curved optical zone 202A (posterior optical zone), a transition zone 202B smoothly connected to and surrounding the posterior optical zone, and an edge zone 202C smoothly connected to and surrounding the transition zone. The two optical zones, the two transition zones, and the two edge zones overlap each other, respectively, in the top view. The transition zones 201B and 202B and the edge zones 201C and 202C are ring shaped in the top view (see FIG. 2C). In preferred embodiments, the diameter of the optical zones is preferably about 5 to 7 mm, and the radial width of the transition zones is preferably about 100 to 1000 µm.

Preferably, for myopia correction, each of the anterior optical zone 201A and posterior optical zone 202A has a spherical or toric shape (i.e. it is a part of a sphere) and is round in the top plan view, and both are convex from the standpoint of the lenticule. In alternative embodiments, the anterior optical zone 201A and the posterior optical zone 202A may have other curved shapes, such as ellipsoidal shapes for correcting myopic astigmatism. The anterior and posterior optical zones 201A and 202A define the optical power of the lenticule and hence the optical power of the refractive power correction after lenticule extraction.

In the embodiment of FIG. 2A, the transition zones 201B and 202B are flat and parallel to each other, and are both parallel to the applanated anterior surface of the cornea. The ring shaped volume defined between the transition zones 201B and 202B is referred to as a plano transition zone of the lenticule because it has a substantially uniform thickness. In preferred embodiments, the thickness of the transition zone of the lenticule is about 10 to 50 µm, or more preferably, 15-40 µm. Note that in this disclosure, the term zone may either refer to a portion of an incision (a 2D surface), or a portion of the lenticule (a 3D volume), depending on context.

In the embodiment shown in FIG. 2A, in the applanated state, the anterior lenticule incision 201 and posterior lenticule incision 202 are mirror symmetrical of each other with respect to an imaginary center plane 204 that is parallel to the applanated anterior corneal surface 203. Thus, the anterior and posterior lenticule incisions provide even refractive power correction. In alternative embodiments (not shown), the anterior and posterior lenticule incisions may have different curvatures and thus provide different corrective powers, but the plano transition zones can still have the same shape as shown in FIG. 2A.

The edge zones 201C and 202C form a smooth edge profile that connect the outer edges of the two transition zones 201B and 202B. The edge zones 201C and 202C intersect each other and may extend beyond their intersection point. The edge zones have a suitable radius of curvature so that the edge of the lenticule has a rounded shape. The rounded shape of the lenticule edge helps to reduce stress concentrations that can arise from sharp corners.

Figure 2B:
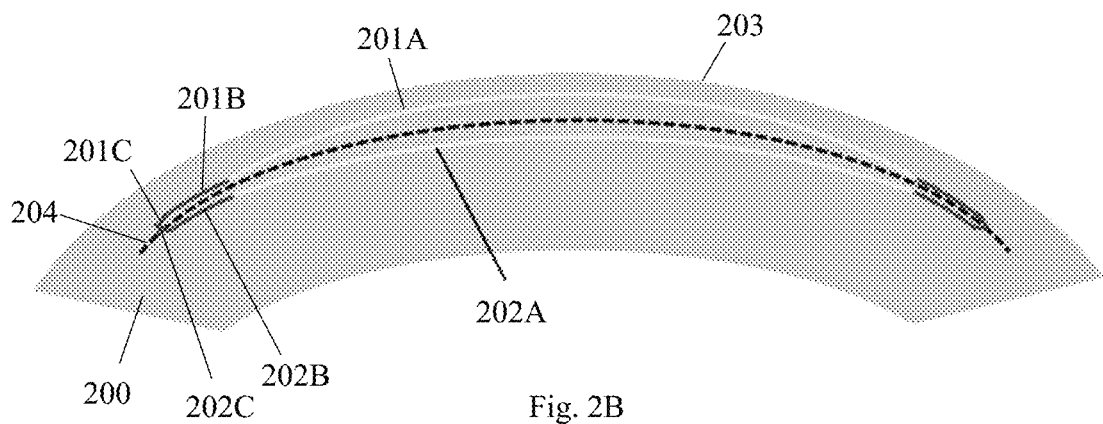
Figure 2C:
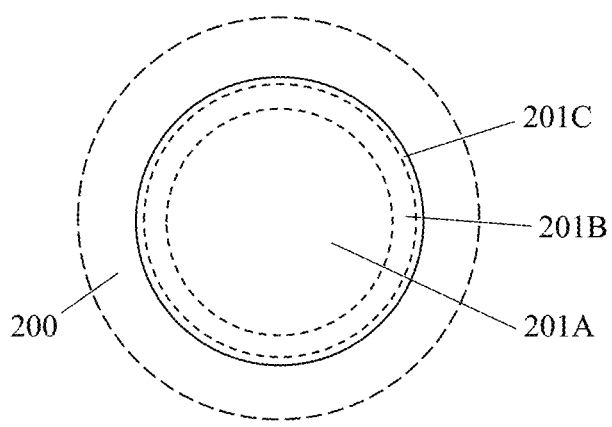

FIG. 2B shows the shape of the incisions in FIG. 2A after the clear contact surface of the patient interface is removed and the cornea is no longer applanated. The imaginary center line 204 is still approximately parallel to the anterior corneal surface 203, which is now curved. It is noted that due to corneal deformation that occurs when the contact lens is removed, the overall size (area) of the anterior surface of the lenticule (the anterior lenticule incision 201) may become larger than the overall size of the posterior surface (the posterior lenticule incision 202).

Figure 3A:
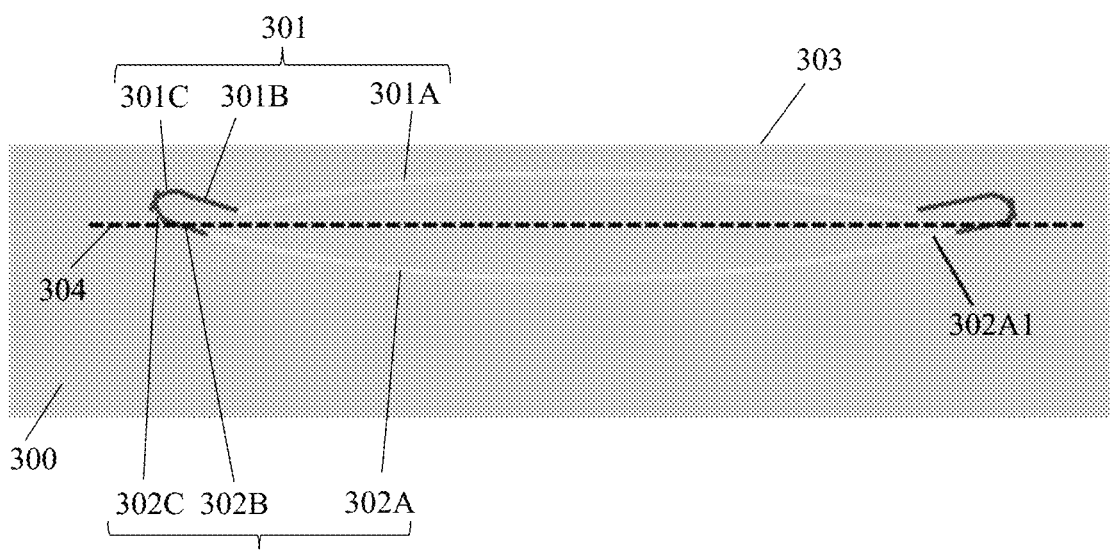
FIGS. 3A-3B illustrate corneal lenticule incisions with a plano transition zone in a lenticule extraction procedure according to another embodiment of the present invention.

FIG. 3A (side cross-sectional view) shows the incisions formed in a corneal lenticule extraction procedure for correcting myopia according to another embodiment of the present invention. Similar to the embodiment shown in FIG. 2A, the cornea 300 is applanated by a patient interface device (not shown). As shown in FIG. 3A, the incisions in cornea 300 include an anterior lenticule incision 301 and a posterior lenticule incision 302. The anterior lenticule incision 301 has a curved optical zone 301A in the center, a transition zone 301B connected to and surrounding the anterior optical zone, and an edge zone 301C connected to and surrounding the transition zone. The posterior lenticule incision 302 has a curved optical zone 302A, a transition zone 302B connected to and surrounding the posterior optical zone, and an edge zone 302C connected to and surrounding the transition zone. In the illustrated embodiment, in the applanated state, the optical zones of the anterior lenticule incision 301 and posterior lenticule incision 302 are mirror symmetrical of each other relative to an imaginary center plane 304 that is parallel to the anterior corneal surface 303, but in alternative embodiments, the optical zones of the anterior and posterior lenticule incisions may have different curvatures and thus different corrective powers.

Figure 3B:
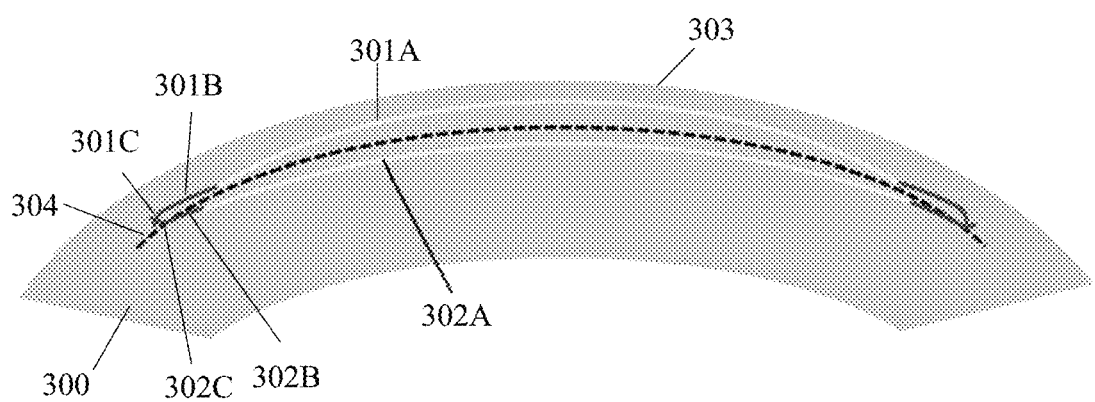

Different from FIG. 2A, in the embodiment of FIG. 3A, the plano transition zones 301B and 302B are angled towards the anterior corneal surface 303 while extending radially outwards. In other words, the transition zones 301B and 302B are still parallel to each other (thus the volume defined between them is still a plano transition zone of the lenticule that has a substantially uniform thickness), but they are not parallel to the anterior corneal surface. This angled shape further promotes the mating of the anterior and posterior lenticule incisions in the optical zone. The angling of the plano transition zone towards the anterior corneal surface also allows for the overall size of the posterior lenticule incision 302 of the lenticule to be increased relative to the anterior lenticule incision 301 (see FIG. 3A, at location 302A1), making the areas of the two cuts more equal after the contact lens is removed (see FIG. 3B). In preferred embodiments, the angle of the plano transition zone with respect to the anterior corneal surface, in the applanated state, is about zero to 30 degrees.

In various embodiments, the plano transition zone may have a uniform radial width along the entire circumference (see FIG. 2C), or a non-uniform radial width. For example, the transition zone may be wider along one transverse axis (an axis perpendicular to the optical axis) than along the other; this may be suitable in particular when the optical zone of the lenticule itself is not a perfect circle (e.g., when it is an ellipse). In different embodiments, the plano transition zone may have a uniform angle relative to the anterior corneal surface along the entire circumference (see FIG. 3A), or different angles at different positions along the circumference. The use of non-uniform transition zone width and/or angle may improve the treatment of astigmatism.

In the embodiments of FIGS. 2A-2C and 3A-3B, the radial width, thickness, radius of curvature of the edge zones, and angle of the plano transition zone may be suitably selected by the surgeon.

Shallow Arcuate Incisions

Corneal arcuate incisions are a currently known and used procedure for treating myopia, with incisions typically being made through more than half the thickness of the stroma to allow for flattening of the central region of the cornea. The creation of deep arcuate incisions near the limbal boundary releases the tension in the cornea generated by intraocular pressure, which allows the anterior surface of the cornea between the incisions to flatten. When arcuate incisions are used to correct myopic astigmatism, a pair of arcuate incisions are typically placed facing each other and spaced apart along the direction of the steep axis of the cornea surface.

Figure 4B:
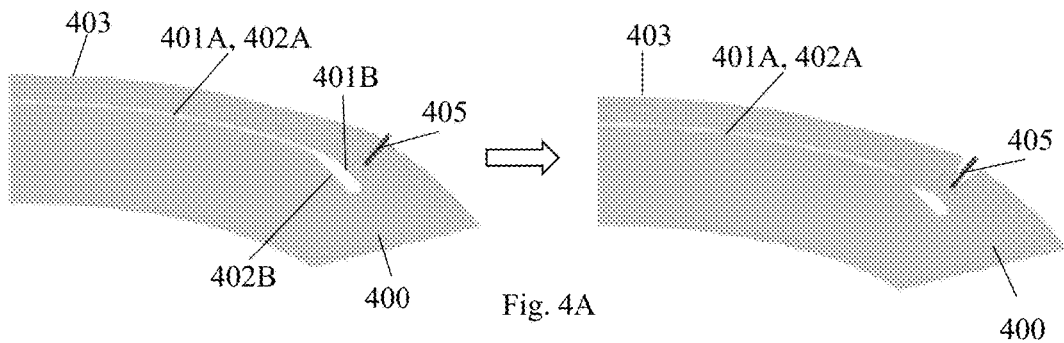
Figure 4B:
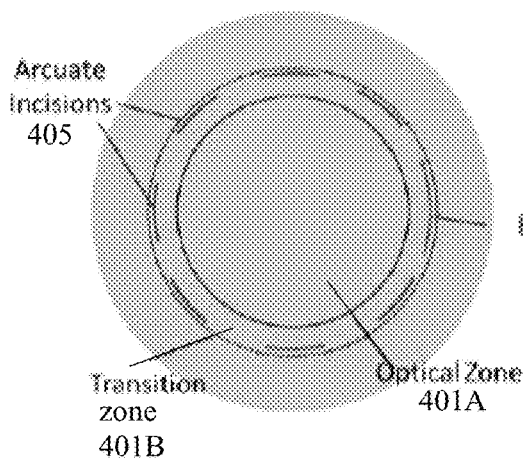
Figure 4C:
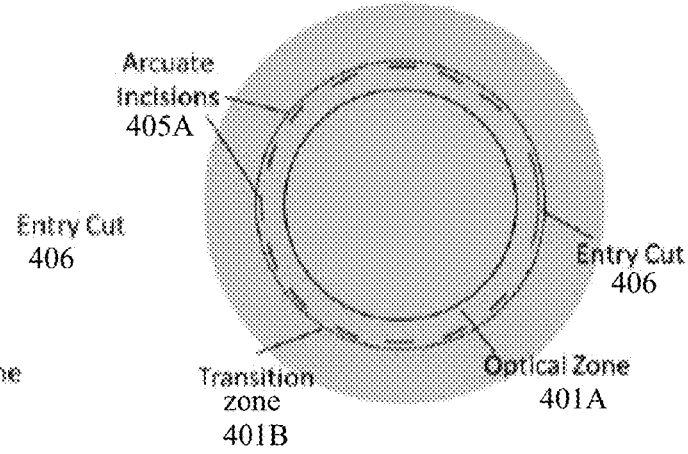

In a second group of embodiments of the present invention, improvements in anterior and posterior surface mating is obtained through the placement of shallow arcuate incisions near the edges of the lenticule, as shown in FIGS. 4A-4C. These incisions can be used with or without the formation of the plano transition zone.

As shown in FIGS. 4A (side cross-sectional view) and 4B (top plan view), a plurality of shallow arcuate incisions 405 are formed from the anterior corneal surface substantially vertically into the remaining corneal tissue above the anterior lenticule incision, near and inside of the edge of the lenticule. The arcuate incisions 405 are shallow in that they extend only partially into the remaining corneal tissue above the anterior lenticule incision without reaching the anterior lenticule incision. In preferred embodiments, the depth of the arcuate incisions 405 is about 50-150 µm, and more preferably, about 100 µm. In preferred embodiments, the arcuate incisions 405 are located on the inside of the outer edge of the lenticule (e.g. where anterior and posterior incisions intersect) at a distance of about 0 to 1 mm from the edge in the top view. In embodiments where the plano transition zone is formed (as shown in FIGS. 4A and 4B), the arcuate incisions 405 are placed at locations that overlap the plano transition zone in the top view.

As shown in the right-hand side diagram of FIG. 4A, the shallow arcuate incisions cause the corneal tissue to form a wedge shaped groove, allowing the corneal tissue to relax, which allows the anterior lenticule surface (cap) to drape over the posterior surface (bed) more freely. This reduces the bulging of the anterior corneal surface as the anterior lenticule surface turns to mate with the posterior surface and alleviate visual aberration at the edges of the optical zone.

In some embodiments, the arcuate incisions 405 are distributed substantially evenly in the angular direction in the top view, along the entirely periphery of the lenticule except for the region where the entry cut 406 is formed. The arc length of the arcuate incisions 405 may be, for example, 5 to 80 degrees, and the angular spacing between them may be, for example, 5 to 85 degrees. FIGS. 4B and 4C show two examples of different angular lengths and spacing of the arcuate incisions 405.

It is noted that the entry cut 406, which is an arcuate cut that reaches the anterior lenticule incision to allow for extraction of the lenticule, also acts to allow the free rotation of the anterior lenticule surface. For practical reasons, the shallow arcuate incisions 405 should have a different length or location to allow for the clear identification of the entry cut 406 by the surgeon. In one alternative embodiment, the shallow arcuate incision is one continuous incision in the angular direction, rather than multiple incisions with spacing in between, and the continuous shallow arcuate incision is separated from the entry cut by a gap on each side.

In alternative embodiments, the shallow arcuate incisions do not need to be evenly distributed in the angular direction. For example, they may be formed only near one transverse axis of the cornea. The spacing and incision depth may also be different in different quadrants of the cornea.

The depths, arc lengths, spacing, and the radial positions of the shallow arcuate incisions 405 may be suitably selected by the surgeon.

In alternative embodiments, the arcuate incisions are made beneath the anterior corneal surface, entirely within the stroma. In such embodiments, the arcuate incisions may have the same locations as the incisions 405/405A shown FIGS. 4A-4C and described above, but they do not reach the corneal surface. Such incisions may have the effect of preventing epithelial ingrowth, while still allowing for the anterior stroma to relax.

The plano transition zone and the shallow arcuate incisions both operate to improve the mating of the anterior and posterior surfaces following lenticule extraction. These techniques may be employed separately or in combination.

Corneal Lenticule Profile with Wider Posterior Cut, Transition Zone and Ring Cut In conventional corneal lenticule extraction procedures, the lenticule cuts are typically made while the cornea is applanated, and in this configuration, the lenticules are cut such that the anterior (cap) and posterior (bed) surfaces have an equal optical power and hence an equal surface area. However, when the applanation is removed from the cornea, the anterior lenticule surface area increases more than the posterior lenticule surface area, because the anterior surface is compressed more during applanation. This can lead to poor surface mating following lenticule extraction, including wrinkling of the anterior lenticule surface. Additionally, gas bubbles may be created during cutting of the posterior surface of the lenticule that become trapped at the edges of the lenticule and can deform the anterior portion of the corneal stroma as it is being cut. This can lead to variation in the achieved lenticule cut depth, increased light scattering, and less predictable visual outcome. Additionally, the trapping of the bubbles at the edge of the lenticule can create tissue bridges at the edges of the optical zone that hinder lenticule extraction.

A third group of embodiments described below provide a lenticule cutting profile that has features that can reduce the afore mentioned problems associated with lenticule cutting and extraction.

Figure 5:
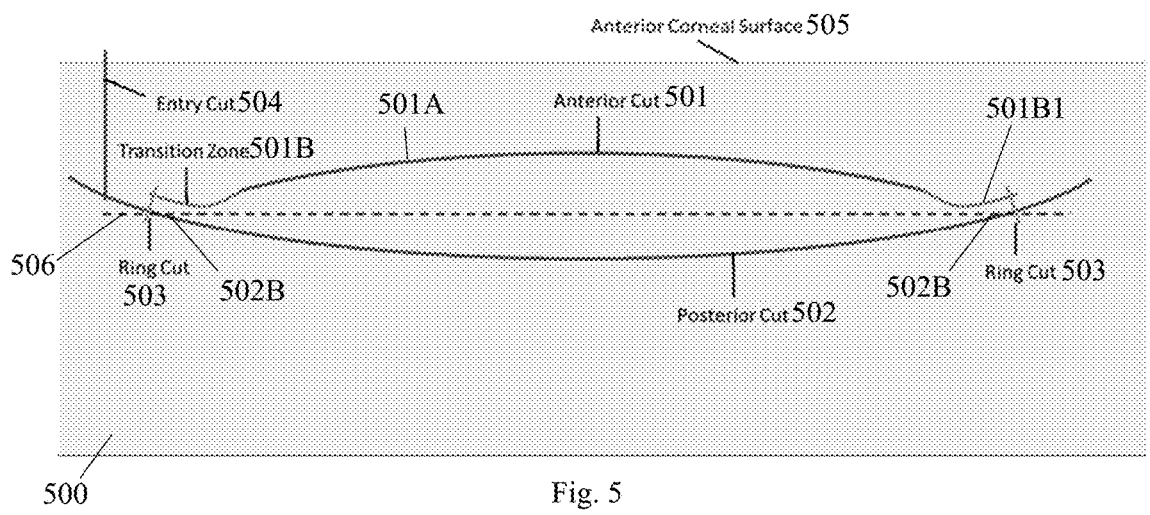
FIGS. 5-14 illustrate corneal lenticule incisions with transition zone, pocket zone, entry extension zone, ring cut, and/or pocket cut in a lenticule extraction procedure according to embodiments of the present invention.

A corneal lenticule cutting profile for a myopic treatment according to the third group of embodiments of the present invention is shown in FIG. 5 (side cross-sectional view). The cornea 500 is applanated by a patient interface device (not shown) during the procedure. The lenticule cutting profile includes an anterior lenticule incision 501, a posterior lenticule incision 502, a ring cut 503, and one or more entry cuts 504. The anterior lenticule incision 501 and the posterior lenticule incision 502 do not intersect each other; the ring cut 503 intersects both the anterior lenticule incision 501 and the posterior lenticule incision 502 (both intersection lines being closed curves) and extends around the entire circumference of the lenticule to form the isolated lenticule volume bound by these three surfaces.

The anterior lenticule incision 501 includes an anterior optical zone 501A in the center and a peripheral transition zone 501B smoothly connected to and surrounding the anterior optical zone. The posterior lenticule incision 502 is a continuous surface (e.g., a continuous spherical surface) and has a wider diameter than the anterior lenticule incision 501 including the anterior transition zone 501B. The portion of the posterior lenticule incision 502 that overlaps the anterior optical zone 501A in the top view is the posterior optical zone 502A, while the area outside of the posterior optical zone is a posterior transition zone 502B. In preferred embodiments, the optical zone 501A of the anterior lenticule incision has a spherical shape and is round in the top plan view (not shown), and the entire posterior lenticule incision 502 has a spherical shape and is round in the top plan view; both are convex from the standpoint of the lenticule. Preferably, the anterior optical zone 501A and posterior optical zone 502A are mirror symmetrical of each other with respect to an imaginary center plane 506 which is parallel to the applanated anterior corneal surface 505. In alternative embodiments, the anterior optical zone 501A and the posterior lenticule incision 502 may have other suitable shapes, as determined by the optical power correction requirements.

The inner edge of the anterior transition zone 501B is smoothly connected to the outer edge of the anterior optical zone 501A. In some embodiments, the portion of the transition zone 501B that connects with the anterior optical zone 501A may be described by a cubic spline with first order continuity to create a smooth transition with the anterior optical zone 501A. As it extends radially outwards, the anterior transition zone 501B initially extends downwardly (away from the applanated anterior corneal surface 505) and then makes a bend to extend upwardly (toward the anterior corneal surface). An outer portion 501B1 of the anterior transition zone 501B matches the curvature of the corresponding portion of the posterior transition zone 502B, with an offset of a specified thickness between them, forming a plano transition zone volume between them. This plano transition zone provides better surface mating of the anterior and posterior surfaces after lenticule removal.

The ring cut 503 extends around the entire lenticule, and intersect both the posterior lenticule incision 502 and the anterior lenticule incision 501 in the transition zones, near the outer edge of the anterior transition zone 501B. In some embodiments, the ring cut 503 extends in a direction perpendicular to the anterior and posterior transition zones 501B and 502B at the locations of intersection. In alternative embodiments, the orientation of the ring cut 503 may deviate from such a perpendicular direction; for example, it may be approximately parallel to the optical axis of the cornea.

The ring cut 503 is a separate incision from the anterior and posterior lenticule incisions. In all embodiments of the present invention, each of the anterior and posterior lenticule incisions may be formed by multiple band-shaped sweeps along meridians of longitude of the lenticule, as described in commonly owned U.S. patent Ser. No. 10/369,052, issued Aug. 6, 2019, entitled "Systems and methods for lenticular laser incision," the disclosure of which is hereby incorporated by references in its entirety. More specifically, a short scan line generated by the high frequency scanner (e.g. the resonant scanner) of the ophthalmic laser is positioned tangential to a parallel of latitude of the lenticule surface, and swept along the a meridian of longitude of the lenticule surface, to form one sweep. A parallel of latitude is a closed curve defined by the intersection of the lenticule with a plane perpendicular to the Z axis (the optical axis); a meridian of longitude is a curve defined by the intersection of the lenticule with a plane that passes through the Z axis (the shape of the anterior and posterior lenticule surfaces shown in various side cross-sectional views of this disclosure is a meridian of longitude). Multiple sweeps along different meridians of longitude around the Z axis collectively form the lenticule surface. The ring cut 503 is formed separately in the sense that it is not formed by parts of the sweeps that form the anterior or posterior lenticule surfaces.

Compared to the embodiment shown in FIG. 3A, where the anterior and posterior lenticule surfaces bend toward each other near the edge and intersect each other to define the outer edge of the lenticule volume, the embodiment of FIG. 5 employs the separate ring cut to define the outer edge of the lenticule volume. The ring cut can reduce tissue bridges at the edges of the lenticule which facilitates easy lenticule extraction. In particular, when the anterior and posterior surfaces are created by multiple band-shaped sweeps along meridians of longitude of the lenticule, such meridian cuts may result in larger spacing in the circumferential direction between the laser pulses at the edges of the lenticule. The ring cut reduces the possibility for tissue bridging at the edges of the lenticule, which facilitates easy and complete extraction of the lenticule without residual tissue.

The entry cut 504 has an arcuate shape in the top plan view (not shown, but refer to FIG. 1B) which spans a predefined angular range, and intersects the posterior lenticule incision 502 at a location outside of the ring cut 503. The entry cut 504 may be perpendicular to the applanated anterior corneal surface, or may be formed at a non-perpendicular angle with respect to the applanated anterior corneal surface.

To form the lenticule incisions, the posterior lenticule incision 502 is cut first, followed by the anterior lenticule incision 501, the ring cut 503, and the entry cut(s) 504 in that order.

In the third group of embodiments, because the posterior lenticule incision 502 is larger than the anterior lenticule incision 501, when the patient interface is removed and the cornea is in the non-applanated state (not shown), the posterior lenticule incision and anterior lenticule incision become approximately equal in size. This improves the mating of the two surfaces after lenticule extraction. Additionally, since the gas bubbles created during cutting of the lenticule migrate to the outer edges of the cuts, the gas bubbles created during the cutting of the posterior lenticule incision will tend to be located further from the optical zone in the center area of the lenticule, which reduces their effect on the cutting of the anterior lenticule surface.

In some alternative embodiments, a plano transition zone is not formed and the transition zone of the top surface overlaps or intersects the bottom cut, allowing for the lenticule to be removed without the ring cut.

Corneal Lenticule Profile with Pocket Zone, Pocket Cut, and Entry Extension

Corneal lenticule cutting profiles according to additional embodiments of the present invention are shown in FIGS. 6-14 (side cross-sectional views, with the cornea in applanated state). In these drawings, like components are designated by like reference symbols, for example: 601, 701, 801, etc. designate the anterior lenticule incision, 601A, 701A, 801A, etc. designate the anterior optical zone, 601B, 701B, 801B, etc. designate the anterior transition zone, 602, 702, 802, etc. designate the posterior lenticule incision, 603, 703, 803, etc. designate the ring cut, 604, 704, 804, etc. designate the entry cut, 1205, 1305, etc. designate the pocket cut, etc.

Figure 6:
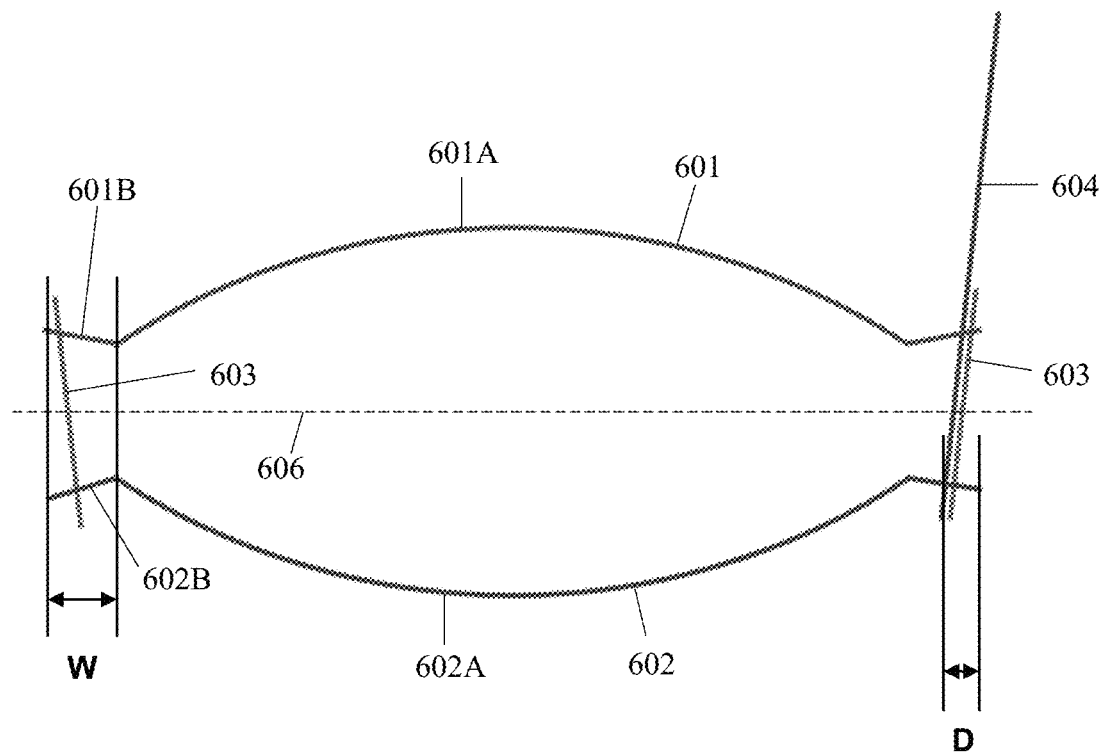
Figure 7:
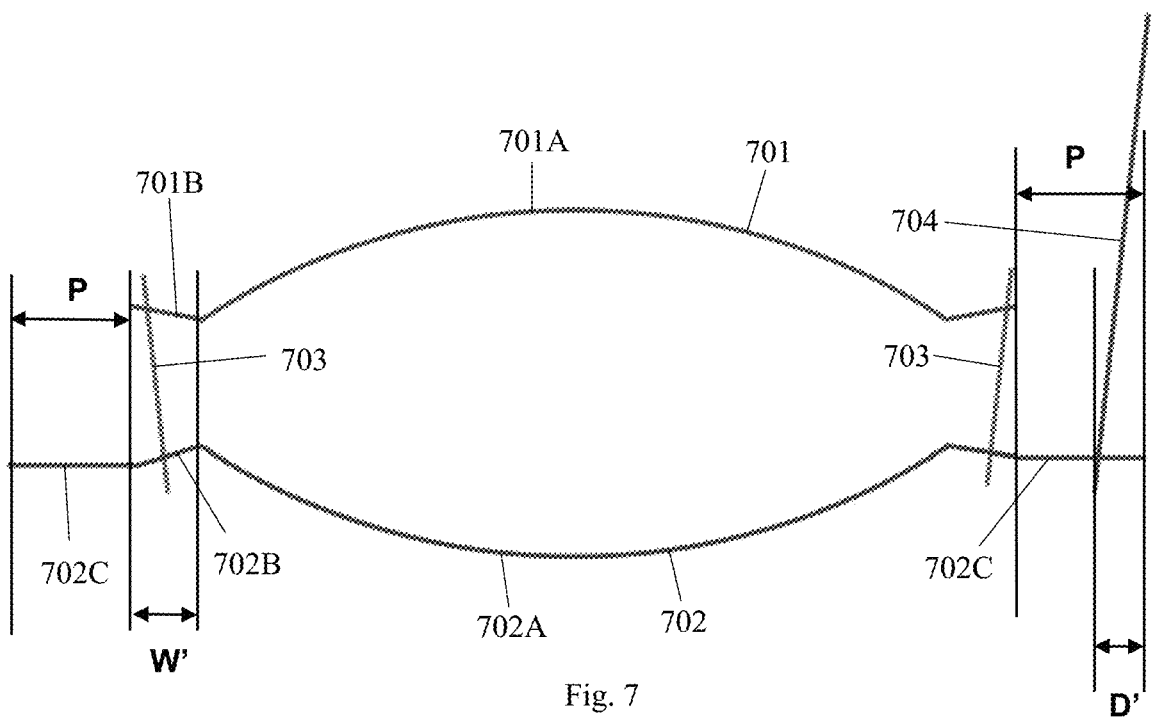
Figure 8:
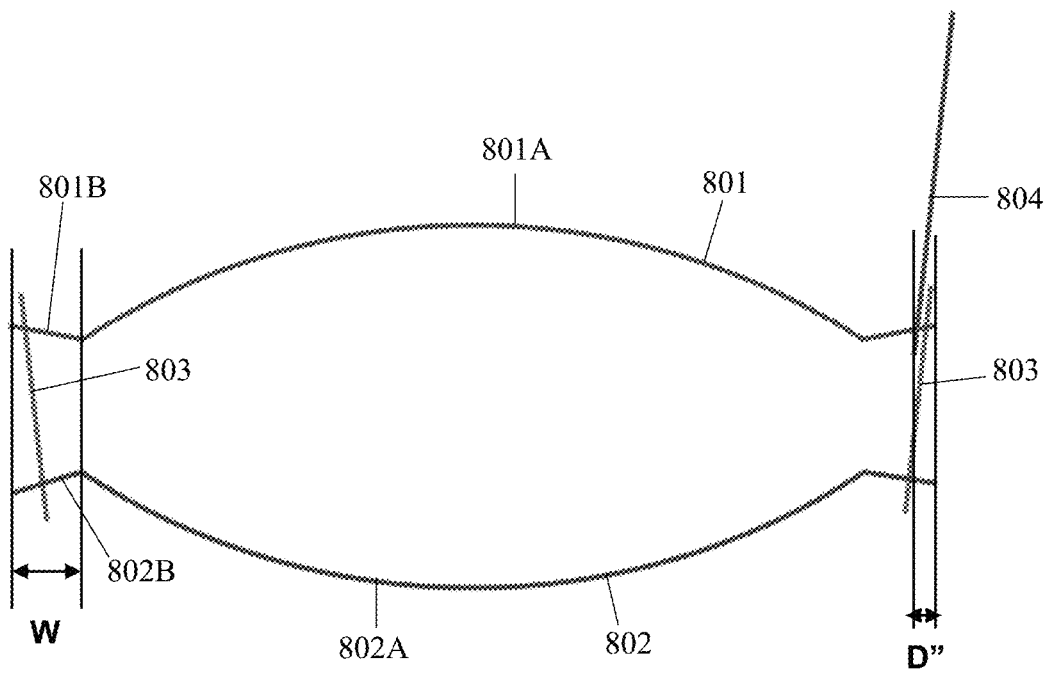
Figure 9:
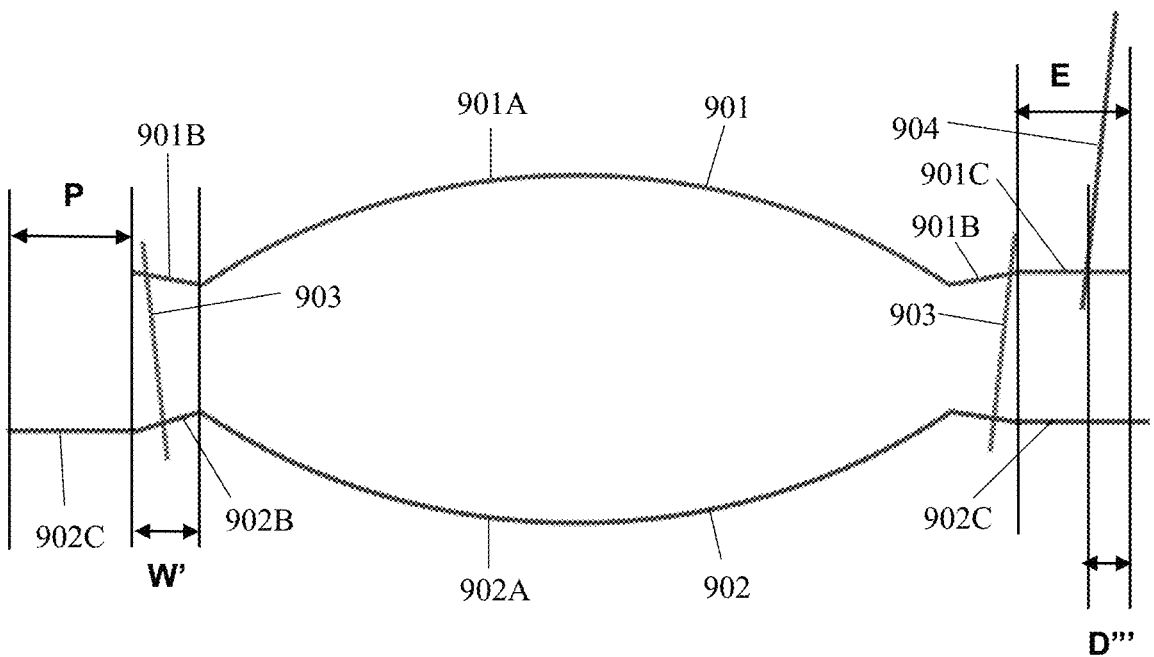

FIGS. 7 and 9 show lenticule cutting profiles where pockets are formed outside of the lenticule edge to allow gas bubbles to migrate away from the central region (the optical zone) of the incisions and into the pockets, while FIGS. 6 and 8 show corresponding corneal lenticule cutting profiles that do not have these pockets.

The lenticule cutting profile shown in FIG. 6 includes an anterior lenticule incision 601, a posterior lenticule incision 602, a ring cut 603, and one or more entry cuts 604. The anterior lenticule incision 601 includes an anterior optical zone 601A in the center and a peripheral transition zone 601B connected to and surrounding the anterior optical zone. The posterior lenticule incision 602 similarly includes a posterior optical zone 602A in the center and a peripheral transition zone 602B connected to and surrounding the posterior optical zone. In the illustrated embodiments, the anterior optical zone 601A and posterior optical zone 602A are both convex from the standpoint of the lenticule and are mirror symmetrical with respect to an imaginary center plane 606 that is parallel to the applanated anterior corneal surface (not shown), but they may alternatively have different curvatures. In preferred embodiments, the anterior lenticule incision 601 and posterior lenticule incision 602 are both round in a top plan view (not shown).

The width W of the transition zone is preferably about 300-500 μm, but can be as wide as 1 mm. As they extend away from the optical zones, the transition zones 601B and 602B of the anterior and posterior lenticule incisions angle away from the imaginary center plane 606, so that the transition zone (the volume between the two transition surfaces) is thicker at the outer edge than at where it joins the optical zone. Preferably, the thickness of the transition zone is between 15-40 μm (more preferably, 30 μm) at the point where it joins the optical zone (the thinnest point), and between 15-40 μm (more preferably, 40 μm) at the outer edge. This gives a thicker edge of the lenticule volume, which facilitates lenticule extraction, without making the entire lenticule thicker.

The ring cut 603, which is a separate cut from the anterior and posterior lenticule incisions, extends around the entire lenticule and intersect both the posterior lenticule incision 602 and the anterior lenticule incision 601 in the transition zones 601A and 601B, near the outer edges of the transition zones. The ring cut 603 may be vertical (i.e. parallel to the optical axis), or preferably form an angle of about 0 to 45 degrees (more preferably, about 30 degrees) with respect to vertical in either direction. An angled ring cut may be easier to form than a strictly vertical cut when using a laser. The advantages of the ring cut 603 are similar to those discussed in connection with the embodiment of FIG. 5.

The entry cut 604 intersects the anterior lenticule incision 601 and the posterior lenticule incision 602 in the transition zones inside of the ring cut 603. The distance D from the intersection point of the entry cut 604 with the posterior lenticule incision 602 to the outer edge of the posterior lenticule incision 602 may be adjusted by the surgeon. The angle of the entry cut 604 relative to the vertical direction is preferably 0 to 50 degrees, and more preferably, about 30 degrees.

To form the lenticule incisions, the posterior lenticule incision 602 is cut first, followed by the ring cut 603, the anterior lenticule incision 601, and the entry cut 604 in that order.

The embodiment shown in FIG. 7 is similar to that shown in FIG. 6, except that (1) the posterior lenticule incision 702 has an additional horizontal ring-shaped pocket zone 702C connected to and surrounding the transition zone 702B; and (2) the entry cut 704 is located in the pocket zone. The anterior lenticule incision 701 does not have such a pocket zone. In the illustrated embodiment, the pocket zone 702C extends substantially horizontally, but it may alternatively extend downwardly or upwardly. The width P of the pocket zone may be 0 to 1 mm (0 meaning there is no pocket zone), and preferably, 100-500 μm. The entry cut 704 is located in the pocket zone, and the distance D' from the intersection point of the entry cut 704 with the posterior lenticule incision 702 to the outer edge of the posterior lenticule incision 702 may be adjusted by the surgeon. In a preferred embodiment, the distance D' is about 90 μm. Due to the presence of the pocket zone 702C, the width of the transition zone 701B and 702B may be reduced, which reduces the overall lenticule volume. In other words, the transition zone width W' in the embodiment of FIG. 7 may be smaller than the transition zone width W in the embodiment of FIG. 6.

Because the posterior lenticule incision 702 is formed first, the pocket zone 702C of the posterior lenticule incision 702 creates a pocket which may be used to guide gas bubbles away from the optical zone when forming the various incisions. Such gas bubbles are formed in the cornea when the laser pulses interact with the corneal tissue to form the incision. Bubble formation is undesirable, as bubbles are typically opaque and can distort the subsequent laser light. The pocket zone 702C in the posterior lenticule incision 702 can allow bubbles to stay in the pocket zone and prevent them from migrating toward the optical zone.

Figure 15:
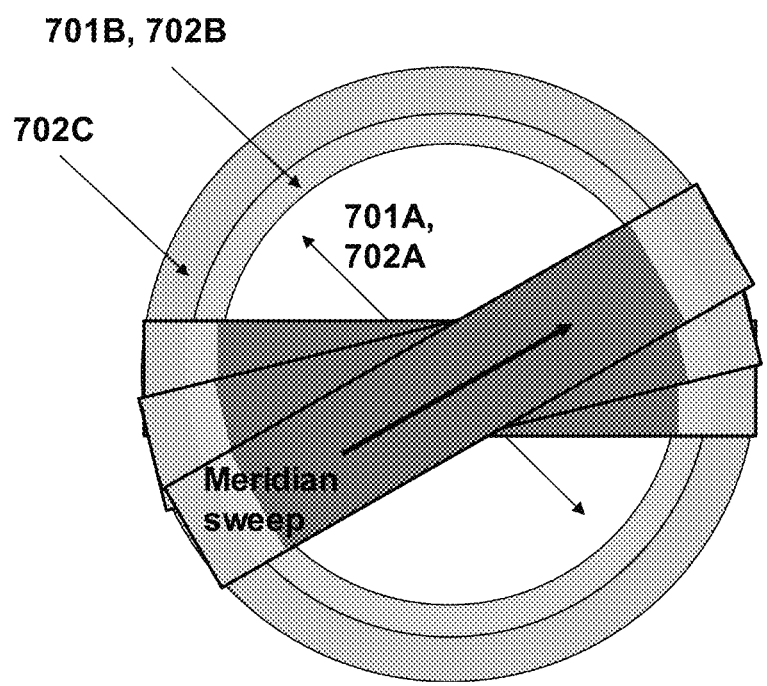
FIG. 15 illustrates a method of cutting a top or bottom lenticule incision using cuts along meridians of longitude of the lenticule.

The pocket zone has other advantages as well. For example, because the posterior lenticule incision 702 is formed by multiple band-shaped sweeps along meridians of longitude of the lenticule (see FIG. 15, top view), the first pulses of laser firing, at the starting end of a meridian sweep, will be in the pocket zone and outside the lenticule volume. Also, high pulse density transitions (when transitioning from one meridian sweep to another) occur outside the lenticule volume.

The embodiment shown in FIG. 8 is similar to that shown in FIG. 6, except that the entry cut 804 only intersect the anterior lenticule incision 801. The distance D″ from the intersection point of the entry cut 804 with the anterior lenticule incision 801 to the outer edge of the anterior lenticule incision 801 may be adjusted by the surgeon.

The embodiment shown in FIG. 9 is similar to that shown in FIG. 7, except that (1) the anterior lenticule incision 901 has an entry extension zone 901C which extends outwardly from the transition zone 901B; and (2) the entry cut 904 only intersect the anterior lenticule incision 901 in the extension zone 901C. The extension zone 901C does not need to extend angularly along the entire periphery of the lenticule, as long as it spans a sufficient angular range to accommodate the entry cut. In the illustrated embodiment, the extension zone 901C extends substantially horizontally, but it may alternatively extend downwardly or upwardly. The width E of the extension zone, and the distance D‴ from the intersection point of the entry cut 904 with the anterior lenticule incision 901 to the outer edge of the extension zone 901C may be adjusted by the surgeon. The extension zone allows the entry cut to intersect the anterior lenticule incision 901.

The embodiments of FIGS. 7, 9 have the following advantages compared to the embodiments of FIGS. 6 and 8. In the embodiments of FIGS. 7 and 9, the entry cut can be made further from the optical zone without increasing the width of the transition zone and hence the volume of the removed tissue. The entry cut can still be made to access the anterior or the posterior lenticule incision, where it will intersect either the pocket zone of the posterior lenticule incision or the entry extension zone of the anterior lenticule incision. These profiles improve the surgeon's ability to grab the lenticule without wrinkling, and reduce the risk of entry cut impacting the optical zone.

Figure 10:
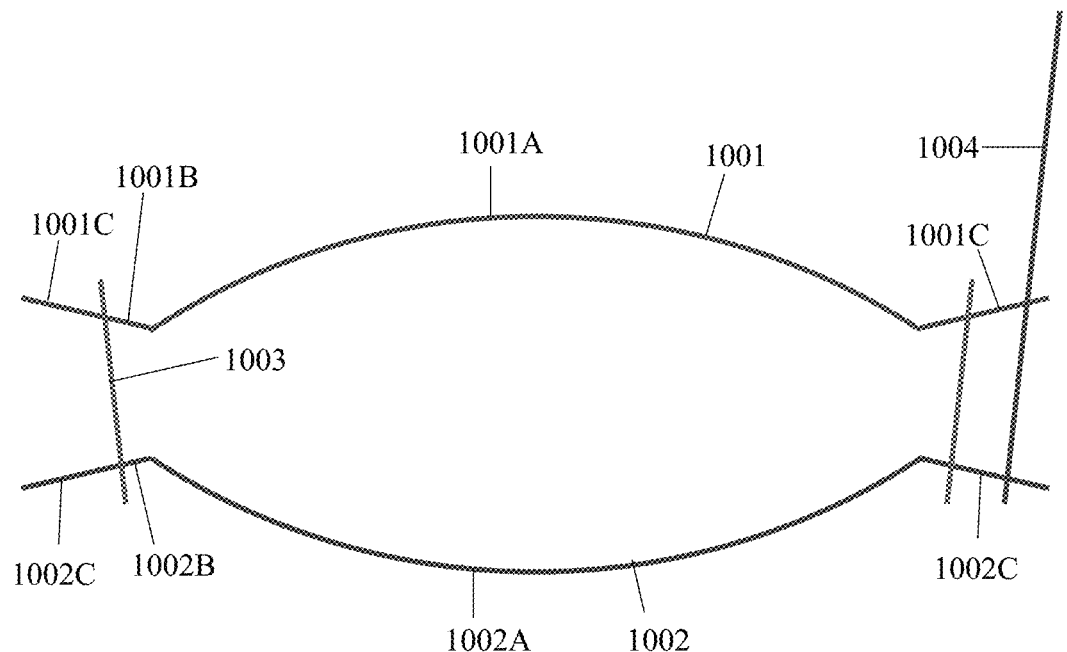

The lenticule profile shown in FIG. 10 is a modification of that shown in FIG. 6, in that the ring cut 1003 is located closer to the optical axis (but still in the transition zones) as compared to the ring cut 603 of FIG. 6. The regions of the anterior and posterior transition zones 1001B and 1002B that are located outside of the ring cut 1003 (and hence outside of the lenticule volume), denoted pocket zones 1001C and 1002C, respectively, form small pockets where the gas bubbles can migrate to. The width of the pocket zone may be up to 1 mm, and preferably, 100-500 μm. The entry cut 1004 remains at a location close to the outer edges of the anterior lenticule incision 1001 and posterior lenticule incision 1002, but now outside of the ring cut 1003.

Figure 11:
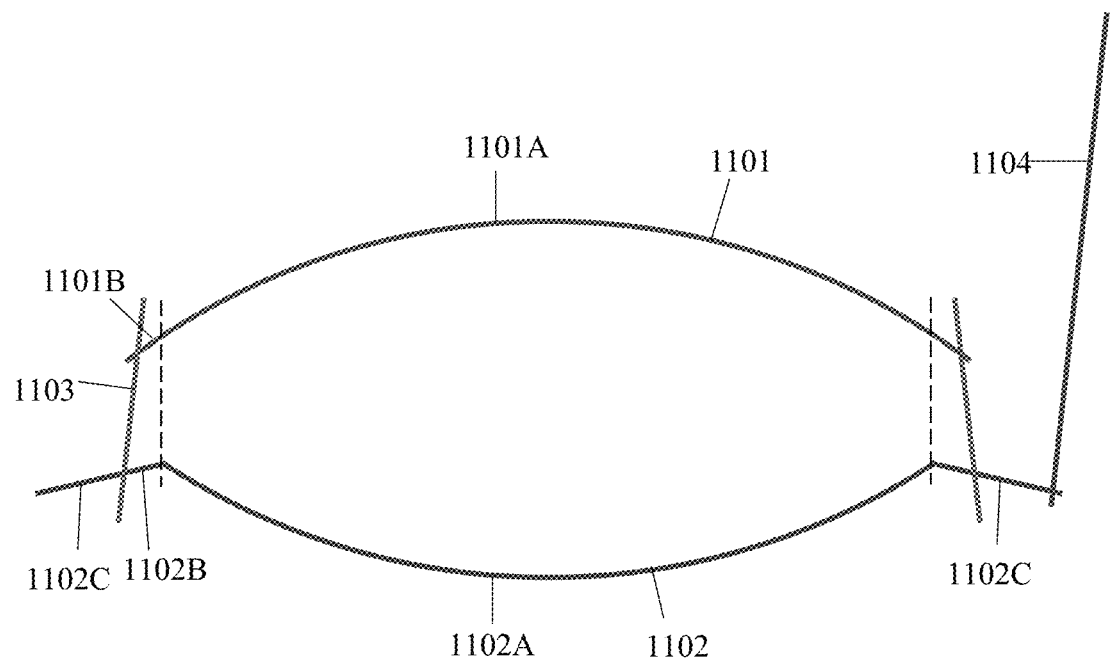

The lenticule profile shown in FIG. 11 is similar to that shown in FIG. 10, except that (1) the anterior lenticule incision 1101 has a different transition zone; and (2) the ring cut 1103 are angled in a different direction. In the embodiment of FIG. 10, the ring cut 1003 has a larger diameter at the top than at the bottom (i.e. it is angled outwardly as it extends in the deep-to-shallow direction), while in the embodiment of FIG. 11, the ring cut 1103 has a smaller diameter at the top than at the bottom (i.e. it is angled inwardly as it extends in the deep-to-shallow direction). The anterior lenticule incision 1101 is a continuous surface (e.g., a continuous spherical surface) with an optical zone 1101A corresponding to the optical zone 1102A of the posterior lenticule incision 1102 (as indicated by the two vertical dashed lines), and a relatively narrow transition zone 1101B which surrounds the optical zone 1101A but does not extend as far as the pocket zone 1102C of the posterior lenticule incision 1102. In other words, the pocket zone is only formed in the posterior lenticule incision 1102. Because of the inward angle of the ring cut 1103, the intersection point of the ring cut 1103 with the anterior lenticule incision 1101 can be located relatively close to the outer edge of the optical zone 1101A, allowing the anterior transition zone 1101B to be relatively narrow. The location of the entry cut 1104 may be the same as that shown in FIG. 11, but it now only intersects the posterior lenticule incision 1102.

Figure 12:
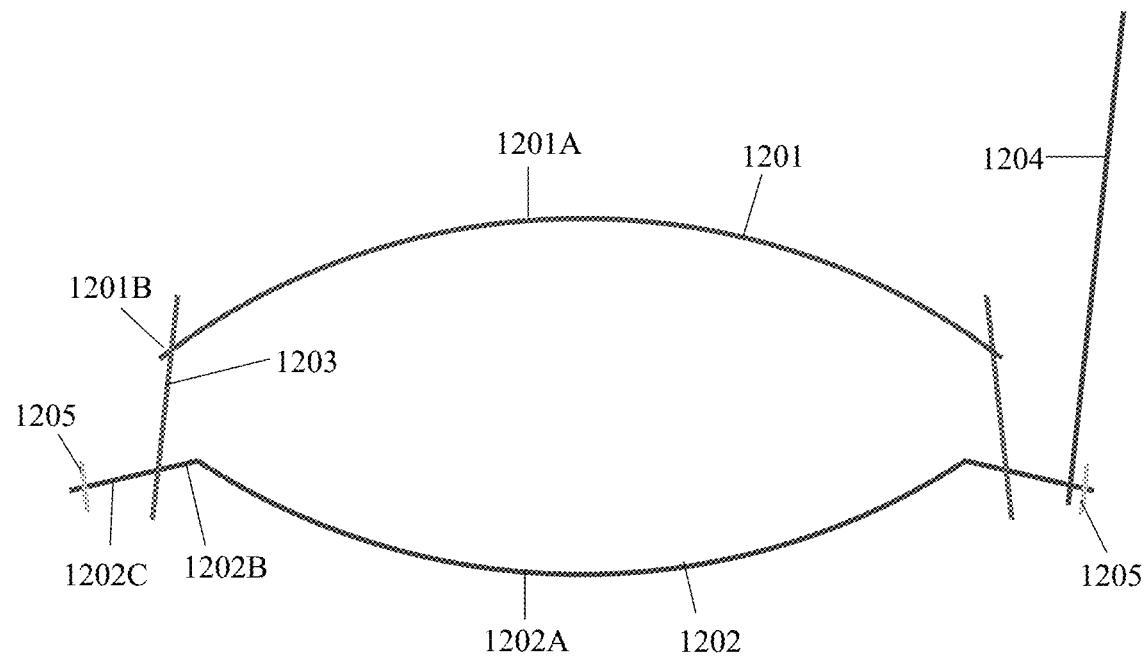

The lenticule profile shown in FIG. 12 is similar to that shown in FIG. 11, with the addition of a separate pocket cut 1205. The pocket cut 1205 is a short ring shaped cut, and located outside of the ring cut 1203 and the entry cut 1204 and intersect the pocket zone 1202C of the posterior lenticule incision 1202 near the outer edge of the pocket zone. The pocket cut 1205 may be vertical, or preferably form an angle of about 0 to 45 degrees (more preferably, about 30 degrees) with respect to vertical in either direction. The pocket cut 1205 may be formed first, before any other cut, or formed after the posterior lenticule incision 1202 but before the other cuts. The pocket cut 1205 allows gas bubbles to migrate away from the optical zone of the incisions and into the pockets it creates.

In alternative embodiments, the separate pocket cut may be added to any of the embodiments of FIGS. 5-11.

Figure 13:
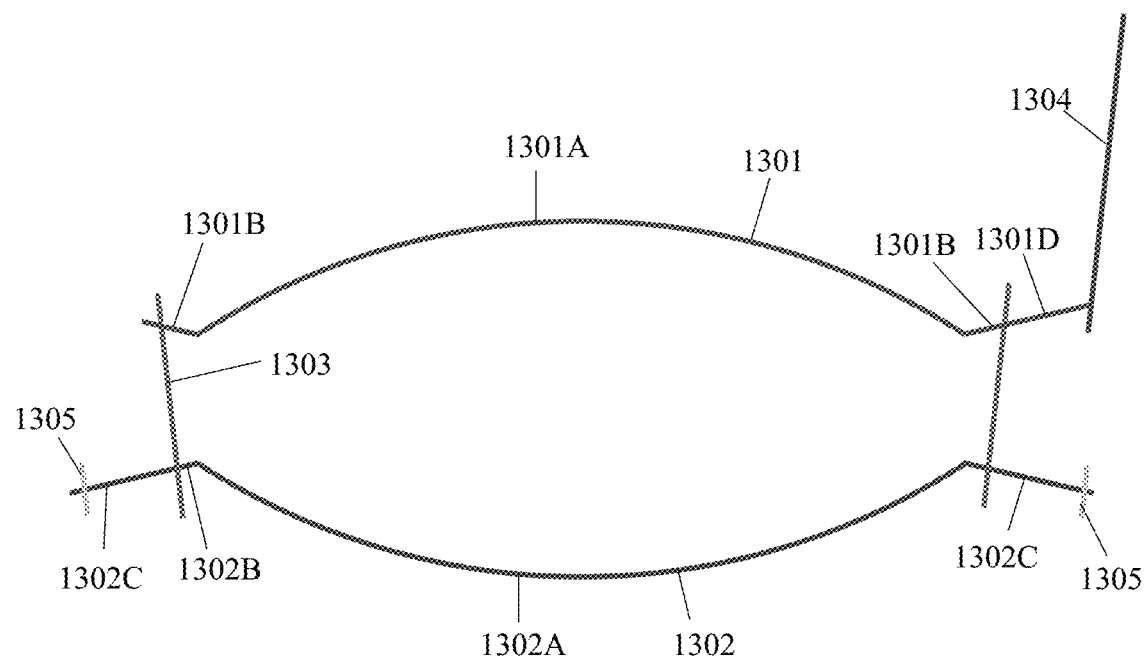

The lenticule profile shown in FIG. 13 is similar to that shown in FIG. 10, except that (1) the anterior lenticule incision 1301 has a transition zone 1301B that is narrower than the transition zone 1302B (including the pocket zone 1302C) of the posterior lenticule incision 1302, i.e., the anterior lenticule incision 1301 does not have a pocket zone; (2) the anterior lenticule incision 1301 has an entry extension zone 1301D outside the transition zone 1301B and spanning a defined angular range less than the full circumference; (3) the entry cut 1304 only intersects the anterior lenticule incision in the extension zone 1301D; and (4) a separate pocket cut 1305 is added, similar to pocket cut 1205 shown in FIG. 12. The cutting order is the same as that of the embodiment of FIG. 12.

Figure 14:
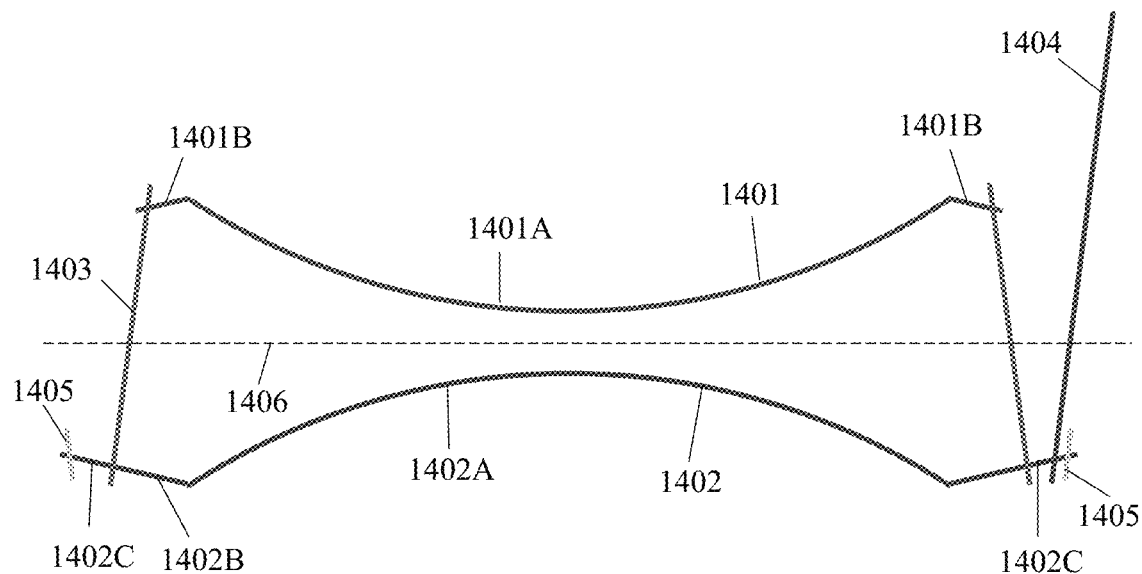

While the embodiments shown in FIGS. 6-13 are configured for myopic treatment, FIG. 14 shows a lenticule profile for hyperopic treatment. The lenticule profile of FIG. 14 includes an anterior lenticule incision 1401, a posterior lenticule incision 1402, a ring cut 1403, an entry cut 1404, and a pocket cut 1405. The anterior and posterior lenticule incisions 1401 and 1402 have concave shapes from the standpoint of the lenticule. The anterior lenticule incision 1401 includes an anterior optical zone 1401A in the center and a peripheral transition zone 1401B connected to and surrounding the anterior optical zone. The posterior lenticule incision 1402 similarly includes a posterior optical zone 1402A in the center and a peripheral transition zone 1402B connected to and surrounding the posterior optical zone. In the illustrated embodiment, the optical zones 1401A and 1402A are mirror symmetrical with respect to an imaginary center plane 1406 that is parallel to the applanated anterior corneal surface (not shown), but they may alternatively have different curvatures. The ring cut 1403 is angled inwardly such that it has a smaller diameter at the top. The posterior transition zone 1402B is wider than the anterior transition zone 1401B, and an outer portion 1402C of the posterior transition zone outside of the ring cut 1403 serves as a pocket zone to allow gas bubbles to migrate away from the optical zones of the incisions and into the pockets. The ring shaped pocket cut 1405 is similar to that of the embodiments of FIGS. 12 and 13. The entry cut 1404 intersects only the posterior lenticule incision 1402, at a location between the ring cut 1403 and the pocket cut 1405. The cutting order is the same as that of the embodiments of FIGS. 12 and 13.

While an exemplary lenticule profile for hyperopic treatment is shown in FIG. 14, other lenticule profile for hyperopic treatment may be formed with various other elements used in the embodiments of FIGS. 5-13, such as pocket zone in the anterior lenticule incision, different angles of the ring cut, entry extension zone in the anterior lenticule incision, etc.

To summarize, in embodiments of the present invention, the various elements of the lenticule incision profiles include: plano transition zone (FIGS. 2A-3B), wider posterior lenticule incision (FIGS. 5, 7, 9, and 11-14), separate ring cut (FIGS. 5-14), ring cut angled inwardly (FIGS. 5, 11, 12, and 14), pocket zone in posterior lenticule incision or both posterior and anterior lenticule incisions (FIGS. 5, 7, and 9-14), extension zone in anterior lenticule incision for entry cut (FIGS. 9 and 13), separate ring shaped pocket cut (FIGS. 12-14), and shallow arcuate incisions on corneal surface (FIGS. 4A-C). These elements may be employed separately or in combination. Each of these elements, alone or in combination with other elements, confers one or more benefits related to better surface mating, reduced bulges near the border after lenticule extraction, better gas bubble management, and easier and/or more complete lenticule extraction, as described in more detail earlier. These advantages ultimately lead to more accurate vision correction and better healing.

While many specific embodiments are described, other embodiments are possible, using other combinations of the various elements described above.

The lenticule cutting profile of embodiments of the present invention may be used to form lenticules to treat myopia (when the lenticule is thicker at the center than the edge), hyperopia (when the lenticule is thinner at the center than the edge), and mixed astigmatism.

It will be apparent to those skilled in the art that various modification and variations can be made in the corneal lenticular incision methods and related apparatus of the present invention without departing from the spirit or scope of the invention. Thus, it is intended that the present invention cover modifications and variations that come within the scope of the appended claims and their equivalents.

What is claimed is:

1. A method for forming a lenticule in a cornea of a patient's eye using an ophthalmic surgical laser system, comprising:
operating the ophthalmic surgical laser system to generate a focused laser beam; and
scanning the laser beam in the cornea to form an anterior lenticule incision and a posterior lenticule incision in the cornea,
wherein the anterior lenticule incision includes a curved anterior optical zone, an anterior transition zone connected to and surrounding the anterior optical zone, and an anterior edge zone connected to and surrounding the anterior transition zone, wherein the posterior lenticule incision includes a curved posterior optical zone, a posterior transition zone connected to and surrounding the posterior optical zone, and a posterior edge zone connected to and surrounding the posterior transition zone, wherein the anterior optical zone and the posterior optical zone overlap each other in a top view along a direction parallel to an optical axis of the eye, the anterior transition zone and the posterior transition zone overlap each other in the top view, and the anterior edge zone and the posterior edge zone overlap each other in the top view,
wherein the anterior and posterior lenticule incisions form the lenticule of corneal tissue between them, wherein the anterior edge zone and the posterior edge zone intersect each other to form an outer edge of the lenticule, and
wherein the anterior transition zone and the posterior transition zone are parallel to each other and form a plano transition zone of the lenticule between them.

2. The method of claim 1, wherein the anterior and posterior optical zones are both convex.

3. The method of claim 1, wherein a radial width of the anterior and posterior transition zones is 100 to 1000 μm and a distance between the anterior and posterior transition zones is 10 to 50 μm.

4. The method of claim 1, wherein the anterior and posterior transition zones are both parallel to an anterior surface of the cornea.

5. The method of claim 1, wherein the anterior and posterior transition zones are both angled toward an anterior surface of the cornea as they extend radially outwards, at an angle of 0 to 30 degrees.

6. The method of claim 5, wherein the anterior and posterior edge zones form a smooth edge profile in a side cross-sectional view.

7. The method of claim 1, further comprising:
scanning the laser beam in the cornea to form a plurality of arcuate incisions in the cornea from an anterior surface of the cornea, wherein the arcuate incisions have arcuate shapes and are located inside of the outer edge of the lenticule in the top view, and wherein the arcuate incisions are substantially perpendicular to the anterior surface of the cornea and extend toward the anterior lenticule incision without intersecting the anterior lenticule incision.

8. A method for forming a lenticule in a cornea of a patient's eye using an ophthalmic surgical laser system, comprising:
operating the ophthalmic surgical laser system to generate a focused laser beam; and
scanning the laser beam in the cornea to form an anterior lenticule incision and a posterior lenticule incision in the cornea, wherein the anterior and the posterior lenticule incisions overlap each other in a top view along a direction parallel to an optical axis of the eye, wherein the anterior and posterior lenticule incisions form the lenticule of corneal tissue between them, and wherein the anterior and posterior lenticule incisions intersect each other to form an outer edge of the lenticule; and
scanning the laser beam in the cornea to form a plurality of arcuate incisions in the cornea from an anterior surface of the cornea, wherein the arcuate incisions have arcuate shapes and are located inside of the outer edge of the lenticule in the top view, and wherein the arcuate incisions are substantially perpendicular to the anterior surface of the cornea and extend toward the anterior lenticule incision without intersecting the anterior lenticule incision.

9. The method of claim 8, wherein a depth of the plurality of arcuate incisions is 50-150 μm from the anterior surface of the cornea.

10. A method for forming a lenticule in a cornea of a patient's eye using an ophthalmic surgical laser system, comprising:

operating the ophthalmic surgical laser system to generate a focused laser beam; and scanning the laser beam in the cornea to form an anterior lenticule incision and a posterior lenticule incision in the cornea, wherein the anterior lenticule incision includes a curved anterior optical zone and an anterior transition zone connected to and surrounding the anterior optical zone, wherein the posterior lenticule incision includes a curved posterior optical zone, a posterior transition zone connected to and surrounding the posterior optical zone, and a posterior pocket zone connected to and surrounding the posterior transition zone, wherein the anterior optical zone and the posterior optical zone overlap each other in a top view along a direction parallel to an optical axis of the eye, and the anterior transition zone and the posterior transition zone overlap each other in the top view without intersection each other, and wherein the posterior lenticule incision is larger than the anterior lenticule incision in the top view;

scanning the laser beam in the cornea to form a ring cut, wherein the ring cut extends along an entire circumference of the lenticule and intersects both the anterior transition zone and the posterior transition zone to form the lenticule of corneal tissue bound by the anterior and posterior lenticule incisions and the ring cut; and scanning the laser beam in the cornea to form an entry cut, wherein the entry cut extends in an angled direction with respect to the optical axis and extends from an anterior corneal surface to intersect either the posterior lenticule incision, or the anterior lenticule incision, or both the posterior lenticule incision and the anterior lenticule incision, and wherein the entry cut extends a predefined angular range in the top view.

11. The method of claim 10, wherein the posterior lenticule incision is formed first, followed by the ring cut, then the anterior lenticule incision, and then the entry cut.

12. The method of claim 10, wherein a radial width of the posterior pocket zone is 30-300 μm.

13. The method of claim 10, wherein the posterior lenticule incision including the posterior optical zone, the posterior transition zone and posterior pocket zone is a spherical surface.

14. The method of claim 13, wherein a ring shaped portion of the anterior transition zone and a corresponding ring shaped portion of the posterior transition zone have matching curvatures and are separated from each other by a predefined distance.

15. The method of claim 13, wherein the ring cut is perpendicular to both the anterior transition zone and the posterior transition zone at respective intersection locations.

16. The method of claim 10, wherein the anterior transition zone and the posterior transition zone are non-parallel to each other, wherein a distance between the anterior transition zone and the posterior transition zone increases as the anterior and the posterior transition zones extend respectively away from the anterior and posterior optical zones.

17. The method of claim 10, wherein the entry cut intersects only the posterior lenticule incision in the posterior pocket zone.

18. The method of claim 10, wherein the anterior lenticule incision further includes an entry extension zone which extends outwardly from the anterior transition zone, wherein the entry extension zone extends a predefined angular range in the top view, wherein the entry cut intersects only intersects the anterior lenticule incision in the anterior entry extension zone, and wherein the predefined angular range of the entry cut is smaller than and located with the angular range of the entry extension zone.

19. The method of claim 10, further comprising:

scanning the laser beam in the cornea to form a pocket cut, wherein the pocket cut extends along an entire circumference of the posterior lenticule incision and intersects only the posterior lenticule incision in the posterior pocket zone.

20. The method of claim 19, wherein the pocket cut is formed first, followed by the posterior lenticule incision, then the ring cut, then the anterior lenticule incision, and then the entry cut; or wherein the posterior lenticule incision is formed first, followed by the pocket cut, then the ring cut, then the anterior lenticule incision, and then the entry cut.

* * * * *